United States Patent [19]
Umezawa et al.

[11] Patent Number: 4,518,532
[45] Date of Patent: May 21, 1985

[54] N-[4-(3-AMINOPROPYL)-AMINOBUTYL]-2-(ω-GUANIDINO-FATTY-ACID-AMIDO)-2-SUBSTITUTED-ETHANAMIDE AND SALT THEREOF

[75] Inventors: Hamao Umezawa; Tomio Takeuchi, both of Tokyo; Shinichi Kondo, Yokohama; Hironobu Iinuma; Daishiro Ikeda, both of Tokyo; Teruya Nakamura, Kusatsu; Akio Fujii, Kamakura, all of Japan

[73] Assignee: Zaidan Hojin Biseibutsu Kagaku Kenkyu Kai, Tokyo, Japan

[21] Appl. No.: 426,372

[22] Filed: Sep. 29, 1982

[30] Foreign Application Priority Data

Oct. 8, 1981 [JP] Japan ................. 56-159503

[51] Int. Cl.³ ............... C07C 129/12; A61K 31/155
[52] U.S. Cl. ................. 260/404.5; 564/157; 564/159; 514/908
[58] Field of Search ............... 564/157, 159; 260/404.5 PA, 404.5 G

[56] References Cited

U.S. PATENT DOCUMENTS 3,799,988  3/1974  Hashimoto et al. ........... 564/159 X
4,416,899  11/1983  Umezawa et al. ............. 424/320
4,430,346  2/1984  Umezawa et al. ............. 564/159 X

FOREIGN PATENT DOCUMENTS 2084999  4/1982  United Kingdom .

OTHER PUBLICATIONS

Shoji et al., Jour. of Antibiotics 29, 390–393, (1976).
Kido et al., ibid. 33, 791–795, (1980).
Takeuchi et al., ibid. 34, 1619–21, (1981).
Umezawa et al., ibid. 34, 1622–24, (1981).
Kondo et al., ibid. 34, 1625–27, (1981).
Kondo et al., Abstracts, International Conference on Trends in Antibiotic Research, Tokyo, Jun. 14, 15, 1982—p. 15.

Primary Examiner—Thomas A. Waltz
Attorney, Agent, or Firm—Robert E. Carnahan

[57] ABSTRACT

N-[4-(3-Aminopropyl)aminobutyl]-2-(ω-guanidino-fatty acid-amido)-2-substituted-ethanamides represented by the general formula

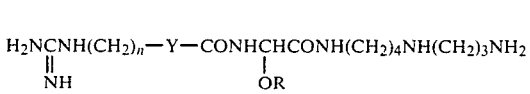

wherein Y represents $-(CH_2-CH_2-)$, $-CH=CH-$ or

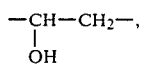

R represents a hydrogen atom, an alkyl group of 1 to 4 carbon atoms which may have a hydroxyl group as substituent, or a benzyl group, and n is an integer of from 1 to 8, provided that when Y is

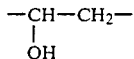

and n is 4, R represents the groups other than the hydrogen atom; a salt thereof having antitumor activity in experimental animal tumors and a process for the preparation thereof is provided.

10 Claims, No Drawings

N-[4-(3-AMINOPROPYL)-AMINOBUTYL]-2-(ω-GUANIDINO-FATTY-ACID-AMIDO)-2-SUBSTITUTED-ETHANAMIDE AND SALT THEREOF

SUMMARY OF THE INVENTION

This invention relates to a novel compound N-[4-(3-aminopropyl)aminobutyl]-2-(ω-guanidino-fatty-acid-amido)-2-substituted-ethanamide which is useful as a carcinostatic substance and is represented by the general formula

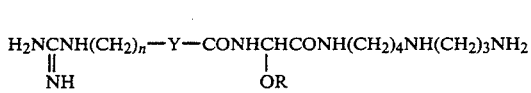

wherein Y represents —CH$_2$—CH$_2$—, —CH=CH— or

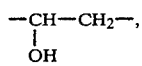

R represents a hydrogen atom, an alkyl group of 1 to 4 carbon atoms which may have a hydroxyl group as substituent, or a benzyl group, and n is an integer of from 1 to 8, provided that when Y is

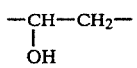

and n is 4, R represents the groups other than the hydrogen atom; a salt thereof and a process for the preparation thereof.

BACKGROUND OF THE INVENTION

During the systematic studies of antitumor antibiotics, a novel antitumor antibiotic BMG 162-aF2, which was named spergualin, was found in a culture filtrate of a strain BMG 162-aF2 (FERM-P 5230; ATCC 31932) of *Bacillus laterosporus* belonging to the genus Bacillus [Takeuchi et al., Journal of Antibiotics, Vol. 34, p. 1619 and p. 1622 (1981), and Umezawa et al., U.S. patent application Ser. No. 297,458 filed Aug. 28, 1981 now U.S. Pat. No. 4,416,899]. The chemical structure of spergualin is represented by the formula

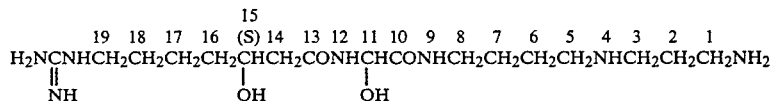

The configuration at the position 15 is S, while that at the position 11 is yet to be determined [Journal of Antibiotics, Vol. 34, 1622 (1981)]. The compound of this formula is synthesized by the condensation of the acid amide and glyoxylylspermidine (Umezawa et al., U.S. patent application Ser. Nos. 375,916, now abandoned, and 375,950, now U.S. Pat. No. 4,430,346, filed May 5 and May 7, 1982, respectively). The resulting epimeric compound is resolved into natural (−)-spergualin and non-natural (+)-spergualin [Journal of Antibiotics, Vol. 34, 1625 (1981)].

DETAILED DESCRIPTION OF THE INVENTION

This invention is based on the discovery that the compounds represented by the general formula I exhibit an excellent antitumor activity in animals. Those wherein R is a group other than a hydrogen atom, have excellent stability relative to those wherein R is a hydrogen atom.

The compounds of general formula I in which R is a hydrogen atom are produced by the condensation of an ω-guanidino fatty acid amide of the general formula

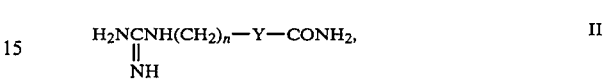

wherein Y and n are as defined above, and N-[4-(3-aminopropyl)aminobutyl]-2,2-dihydroxyethanamide of the formula

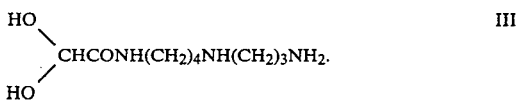

In the case where R of the general formula I is a group other than hydrogen, the compounds are synthesized by reacting the compound obtained by the above condensation or spergualin obtained from the microbial culture filtrate, in which the amino and imino groups may be protected, with an aliphatic mono- or dialcohol of 1 to 4 carbon atoms, a diazoparaffin of 1 to 4 carbon atoms, or benzyl alcohol, and removing the amino or imino protective groups when present.

The compounds of this invention are used generally in the form of a pharmacologically acceptable acid addition salt. As examples of acid addition salts, mention may be made of salts with inorganic acids such as hydrochloric acid, sulfuric acid, phosphoric acid and boric acid, and organic acids such as acetic acid, citric acid, tartaric acid and glutaric acid.

The compounds of this invention represented by the general formula

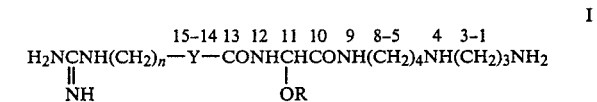

wherein Y, R and n are as defined above, each has an asymmetric carbon at the position 11 and, hence, exists in the form of epimers with respect to carbon 11, that is, in the form of levorotatory epimer [hereinafter referred to as (−)] and in the form of dextrorotatory epimer [hereinafter referred to as (+)]. Unless specifically indicated, the present compound is a mixture (approximately 1:1) of a pair of epimers [if necessary, referred to as (±)].

When Y is —$\overset{15}{\text{CH}}$—$\overset{14}{\text{CH}_2}$—, the compound has also an asymmetric
       |
       OH carbon at position 15 and, hence, there is one epimer having S-configuration at the position 15 and the other epimer having R-configuration at the position 15. Unless specifically indicated, the present compound is a mixture (approximately 1:1) of (S)-epimer and (R)-epimer.

The physicochemical and biological properties of typical examples of the compounds of this invention are as shown below.

(1) Physicochemical properties.

The names of typical compounds of this invention are as shown in Table 1. The molecular formulas and elementary analyses of hydrochlorides of these compounds are summarized in Table 2, and the infrared spectra (KBr tablet) and proton-NMR spectra (in deutero-methanol, tetramethylsilane=TMS as internal standard) in Table 3. The specific rotations of optical isomers of several compounds of this invention are shown in Table 4.

The chemical stability of the present compound was evaluated by determining the retention (%) after heating at 60° C. for 4 hours. In Table 5 are shown the test results together with those for spergualin as reference. The retention was determined by means of high performance liquid chromatography (HPLC). The column was packed with Nucleosil ® 5C18. The solvent used for spergaulin was a mixture (6:94) of acetonitrile—0.01M sodium pentanesulfonate+0.01M Na$_2$HPO$_4$ (pH 3), while that for the compounds of this invention was a mixture of acetonitrile—0.005M sodium pentanesulfonate+0.01M Na$_2$HPO$_4$ (pH 3). The mixing ratio in the latter case was varied for each particular compound. For instance, a mixing ratio of 10:90 was used for Compound No. 9, while that of 7:93 for Compound No. 22.

TABLE 1

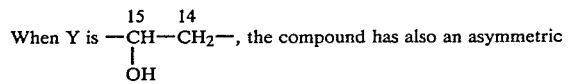

| Compound No. | n | Y | R | Name of Compound |
|---|---|---|---|---|
| 1 | 1 | CH$_2$CH$_2$ | H | N—[4-(3-aminopropyl)-aminobutyl]-2-(4-guanidinobutanamido)-2-hydroxyethanamide |
| 2 | 2 | " | " | N—[4-(3-aminopropyl)-aminobutyl]-2-(5-guanidinopentanamido)-2-hydroxyethanamide |
| 3 | 3 | " | " | N—[4-(3-aminopropyl)-aminobutyl]-2-(6-guanidinohexanamido)-2-hydroxyethanamide |
| 4 | 4 | " | " | N—[4-(3-aminopropyl)-aminobutyl]-2-(7-guanidinoheptanamido)-2-hydroxyethanamide |
| 5 | 5 | " | " | N—[4-(3-aminopropyl)-aminobutyl]-2-(8-guanidinooctanamido)-2-hydroxyethanamide |
| 6 | 6 | " | " | N—[4-(3-aminopropyl)-aminobutyl]-2-(9-guanidinononanamido)-2-hydroxyethanamide |
| 7 | 1 | " | CH$_3$ | N—[4-(3-aminopropyl)-aminobutyl]-2-(4-guanidinobutanamido)-2-methoxyethanamide |
| 8 | 3 | " | " | N—[4-(3-aminopropyl)-aminobutyl]-2-(6-guanidinohexanamido)-2-methoxyethanamide |
| 9 | 4 | " | " | N—[4-(3-aminopropyl)-aminobutyl]-2-(7-guanidinoheptanamido)-2-methoxyethanamide |
| 10 | 5 | " | " | N—[4-(3-aminopropyl)-aminobutyl]-2-(8-guanidinooctanamido)-2-methoxyethanamide |
| 11 | 6 | " | " | N—[4-(3-aminopropyl)-aminobutyl]-2-(9-guanidinononanamido)-2-methoxyethanamide |
| 12 | 4 | " | CH$_2$CH$_3$ | N—[4-(3-aminopropyl)-aminobutyl]-2-(7-guanidinoheptanamido)-2-ethoxyethanamide |
| 13 | 4 | " | CH$_2$CH$_2$—CH$_2$CH$_3$ | N—[4-(3-aminopropyl)-aminobutyl]-2-(7-guanidinoheptanamido)-2-butoxyethanamide |
| 14 | 4 | " | CH$_2$CH$_2$OH | N—[4-(3-aminopropyl)-aminobutyl]-2-(7-guanidinoheptanamido)-2-(2-hydroxy)ethoxyethanamide |
| 15 | 4 | " | CH$_2$—C$_6$H$_5$ | N—[4-(3-aminopropyl)-aminobutyl]-2-(7-guanidinoheptanamido)-2-benzyloxyethanamide |
| 16 | 4 | CH=CH | H | N—[4-(3-aminopropyl)-aminobutyl]-2-(7-guanidino-2-heptenamido)-2-hydroxyethanamide |
| 17 | 5 | " | " | N—[4-(3-aminopropyl)-aminobutyl]-2-(8-guanidino-2-octenamido)-2-hydroxyethanamide |
| 18 | 6 | " | " | N—[4-(3-aminopropyl)-aminobutyl]-2-(9-guanidino-2-nonenamido)-2-hydroxyethanamide |
| 19 | 4 | " | CH$_3$ | N—[4-(3-aminopropyl)-aminobutyl]-2-(7-guanidino-2-heptenamido)-2-methoxyethanamide |
| 20 | 5 | CHCH$_2$<br>\|<br>OH | H | N—[4-(3-aminopropyl)-aminobutyl]-2-(8-guanidino-3-hydroxyoctanamido)-2-hydroxyethanamide |
| 21 | 6 | CHCH$_2$<br>\|<br>OH | " | N—[4-(3-aminopropyl)-aminobutyl]-2-(9-guanidino-3-hydroxynonanamido)-2-hydroxyethanamide |

TABLE 1-continued

H$_2$NCNH(CH$_2$)$_n$—Y—CONHCHCONH(CH$_2$)$_4$NH(CH$_2$)$_3$NH$_2$
∥                                          |
NH                                        OR

| Compound No. | n | Y | R | Name of Compound |
|---|---|---|---|---|
| 22* | 4 | (S) CHCH$_2$<br>     \|<br>    OH | CH$_3$ | N—[4-(3-aminopropyl)-aminobutyl]-2-(7-guanidino-3-hydroxyheptan-amido)-2-methoxy-ethanamide |
| 23* | 4 | " | CH$_2$CH$_3$ | N—[4-(3-aminopropyl)-aminobutyl]-2-(7-guanidino-3-hydroxyheptan amido)-2-ethoxy-ethanamide |
| 24* | 4 | " | CH$_2$CH$_2$—CH$_2$CH$_3$ | N—[4-(3-aminopropyl)-aminobutyl]-2-(7-guanidino-3-hydroxyheptan amido)-2-butoxy-ethanamide |
| 25* | 4 | " | CH$_2$CH$_2$OH | N—[4-(3-aminopropyl)-aminobutyl]-2-(7-guanidino-3-hydroxyheptan amido)-2-(2-hydroxy)-ethoxyethanamide |
| 26* | 4 | " | CH$_2$C$_6$H$_5$ | N—[4-(3-aminopropyl)-aminobutyl]-2-(7-guanidino-3-hydroxyheptan amido)-2-benzyloxy-ethanamide |

*Those compounds of general formula I in which Y is 
$$-\underset{\underset{OH}{|}}{\overset{(S)}{C}}HCH_2-,$$
n is 4, and R is a group other than the hydrogen atom are hereinafter referred to briefly as 11-O-substituted spergualins.

TABLE 2

| Compound No. | Molecular Formula | | Composition Elementary Analysis (%) | | | |
|---|---|---|---|---|---|---|
| | | | C | H | N | Cl |
| 1 | C$_{14}$H$_{31}$N$_7$O$_3$.3HCl.3/2H$_2$O | Calcd. | 34.90 | 7.74 | 20.35 | 22.07 |
| | | Found | 34.92 | 7.87 | 20.21 | 21.96 |
| 2 | C$_{15}$H$_{33}$N$_7$O$_3$.3HCl.3/2H$_2$O | Calcd. | 36.33 | 7.93 | 19.77 | 21.45 |
| | | Found | 36.27 | 8.05 | 19.68 | 21.30 |
| 3 | C$_{16}$H$_{35}$N$_7$O$_3$.3HCl.3/2H$_2$O | Calcd. | 37.69 | 8.10 | 19.23 | 20.86 |
| | | Found | 37.83 | 8.38 | 19.18 | 20.67 |
| 4 | C$_{17}$H$_{37}$N$_7$O$_3$.3HCl.3/2H$_2$O | Calcd. | 38.97 | 8.27 | 18.71 | 20.30 |
| | | Found | 39.10 | 8.42 | 18.57 | 20.18 |
| 5 | C$_{18}$H$_{39}$N$_7$O$_3$.3HCl.3/2H$_2$O | Calcd. | 40.19 | 8.43 | 18.23 | 19.77 |
| | | Found | 40.31 | 8.74 | 17.96 | 19.51 |
| 6 | C$_{19}$H$_{41}$N$_7$O$_3$.3HCl.3/2H$_2$O | Calcd. | 41.34 | 8.58 | 17.76 | 19.27 |
| | | Found | 41.32 | 8.79 | 17.65 | 19.13 |
| 7 | C$_{15}$H$_{33}$N$_7$O$_3$.3HCl.3/2H$_2$O | Calcd. | 36.33 | 7.93 | 19.77 | 21.45 |
| | | Found | 36.41 | 8.10 | 19.45 | 21.32 |
| 8 | C$_{17}$H$_{37}$N$_7$O$_3$.3HCl.3/2H$_2$O | Calcd. | 38.97 | 8.27 | 18.71 | 20.30 |
| | | Found | 39.20 | 8.31 | 18.48 | 20.11 |
| 9 | C$_{18}$H$_{39}$N$_7$O$_3$.3HCl.3/2H$_2$O | Calcd. | 40.19 | 8.43 | 18.23 | 19.77 |
| | | Found | 40.33 | 8.51 | 18.08 | 20.11 |
| 10 | C$_{19}$H$_{41}$N$_7$O$_3$.3HCl.3/2H$_2$O | Calcd. | 41.34 | 8.58 | 17.76 | 19.27 |
| | | Found | 41.39 | 8.82 | 17.62 | 19.15 |
| 11 | C$_{20}$H$_{43}$N$_7$O$_3$.3HCl.3/2H$_2$O | Calcd. | 42.44 | 8.73 | 17.32 | 18.79 |
| | | Found | 42.51 | 8.92 | 17.33 | 18.50 |
| 12 | C$_{19}$H$_{41}$N$_7$O$_3$.3HCl.3/2H$_2$O | Calcd. | 41.34 | 8.58 | 17.76 | 19.27 |
| | | Found | 41.44 | 8.75 | 17.59 | 19.11 |
| 13 | C$_{21}$H$_{45}$N$_7$O$_3$.3HCl.3/2H$_2$O | Calcd. | 43.48 | 8.86 | 16.90 | 18.34 |
| | | Found | 43.61 | 9.04 | 16.78 | 18.43 |
| 14 | C$_{19}$H$_{41}$N$_7$O$_4$.3HCl.3/2H$_2$O | Calcd. | 40.18 | 8.34 | 17.26 | 18.73 |
| | | Found | 40.07 | 8.39 | 17.31 | 18.58 |
| 15 | C$_{21}$H$_{43}$N$_7$O$_3$.3HCl.3/2H$_2$O | Calcd. | 46.94 | 8.04 | 15.97 | 17.32 |
| | | Found | 47.03 | 8.20 | 15.76 | 17.12 |
| 16 | C$_{17}$H$_{35}$N$_7$O$_3$.3HCl.3/2H$_2$O | Calcd. | 39.12 | 7.92 | 18.79 | 20.38 |
| | | Found | 39.10 | 8.02 | 19.05 | 20.07 |
| 17 | C$_{18}$H$_{37}$N$_7$O$_3$.3HCl.3/2H$_2$O | Calcd. | 40.34 | 8.09 | 18.29 | 19.85 |
| | | Found | 40.53 | 8.22 | 18.26 | 19.69 |
| 18 | C$_{19}$H$_{39}$N$_7$O$_3$.3HCl.3/2H$_2$O | Calcd. | 41.49 | 8.25 | 17.83 | 19.34 |
| | | Found | 41.46 | 8.07 | 17.93 | 19.20 |
| 19 | C$_{18}$H$_{37}$N$_7$O$_3$.3HCl.3/2H$_2$O | Calcd. | 40.34 | 8.09 | 18.29 | 19.85 |
| | | Found | 40.09 | 7.86 | 18.11 | 19.71 |
| 20 | C$_{18}$H$_{39}$N$_7$O$_4$.3HCl.3/2H$_2$O | Calcd. | 39.03 | 8.19 | 17.70 | 19.20 |
| | | Found | 38.77 | 8.05 | 17.64 | 20.41 |
| 21 | C$_{19}$H$_{41}$N$_7$O$_4$.3HCl.3/2H$_2$O | Calcd. | 40.18 | 8.34 | 17.26 | 18.73 |
| | | Found | 40.41 | 8.60 | 17.35 | 18.58 |
| 22 | C$_{18}$H$_{39}$N$_7$O$_4$.3HCl.3/2H$_2$O | Calcd. | 39.03 | 8.19 | 17.70 | 19.20 |
| | | Found | 39.03 | 8.50 | 17.49 | 19.15 |
| 23 | C$_{19}$H$_{41}$N$_7$O$_4$.3HCl.3/2H$_2$O | Calcd. | 40.18 | 8.34 | 17.26 | 18.73 |
| | | Found | 40.23 | 8.75 | 17.17 | 18.35 |
| 24 | C$_{21}$H$_{45}$N$_7$O$_4$.3HCl.3/2H$_2$O | Calcd. | 42.32 | 8.62 | 16.45 | 17.84 |
| | | Found | 42.37 | 8.90 | 16.31 | 17.74 |

TABLE 2-continued

| Compound No. | Composition Molecular Formula | Elementary Analysis (%) | | C | H | N | Cl |
|---|---|---|---|---|---|---|---|
| 25 | $C_{19}H_{41}N_7O_5.3HCl.3/2H_2O$ | Calcd. | | 39.08 | 8.11 | 16.79 | 18.21 |
|  |  | Found | | 39.15 | 8.26 | 16.42 | 18.10 |
| 26 | $C_{24}H_{43}N_7O_4.3HCl.3/2H_2O$ | Calcd. | | 45.75 | 7.84 | 15.56 | 16.88 |
|  |  | Found | | 45.77 | 7.93 | 15.39 | 16.64 |

TABLE 3

| Compound No. | Infrared Absorption Spectrum (cm$^{-1}$) | Spectra Proton-NMR Spectrum (δ value) |
|---|---|---|
| 1 | 3320, 2950, 1665, 1525, 1460, 1365, 1260, 1160, 1115, 1070 | 1.4~2.4 (CH$_2$ × 4), 2.40 (CH$_2$), 2.9~3.4 (NCH$_2$ × 5), 5.55 (CH) |
| 2 | 3400, 2950, 1660, 1530, 1465, 1170, 1120, 1080, 1020. | 1.9~2.0 (CH$_2$ × 4), 2.0~2.5 (CH$_2$ × 2) 2.9~3.4 (NCH$_2$ × 5), 5.53 (CH) |
| 3 | 3270, 2950, 1660, 1530, 1460, 1370, 1240, 1165, 1120, 1080 | 1.4~2.0 (CH$_2$ × 5), 2.0~2.5 (CH$_2$ × 2), 2.9~3.4 (NCH$_2$ × 5), 5.52 (CH) |
| 4 | 3400, 2950, 1653, 1525, 1460, 1360, 1160, 1120, 1080 | 1.2~2.0 (CH$_2$ × 6), 2.24 (CH$_2$), 2.30 (CH$_2$), 2.9~3.4 (NCH$_2$ × 5), 5.56 (CH) |
| 5 | 3330, 2925, 1655, 1520, 1460, 1360, 1160. 1120, 1080 | 1.2~2.0 (CH$_2$ × 7), 2.0~2.4 (CH$_2$ × 2), 2.9~3.4 (NCH$_2$ × 5), 5.52 (CH) |
| 6 | 3370, 2925, 1655, 1520, 1460, 1155, 1115, 1080 | 1.2~2.0 (CH$_2$ × 8), 2.0~2.4 (CH$_2$ × 2), 2.9~3.4 (NCH$_2$ × 5), 5.50 (CH) |
| 7 | 3400, 2930, 1650, 1520, 1460, 1360, 1190, 1160, 1090 | 1.4~2.4 (CH$_2$ × 4), 2.40 (CH$_2$), 2.8~3.4 (NCH$_2$ × 5), 2.38 (OCH$_3$), 5.30 (CH) |
| 8 | 3420, 2940, 1650, 1520, 1460, 1355, 1190, 1160, 1090 | 1.4~2.0 (CH$_2$ × 5), 2.0~2.5 (CH$_2$ × 2), 2.9~3.4 (NCH$_2$ × 5), 3.38 (OCH$_3$), 5.29 (CH) |
| 9 | 3420, 2950, 1650, 1520, 1460, 1360, 1190, 1160, 1090 | 1.2~2.0 (CH$_2$ × 6), 2.0~2.5 (CH$_2$ × 2), 2.9~3.4 (NCH$_2$ × 5), 3.37 (OCH$_3$), 5.26 (CH) |
| 10 | 3400, 2925, 1650, 1520, 1455, 1355, 1250, 1190, 1160, 1090 | 1.2~2.0 (CH$_2$ × 7), 2.0~2.5 (CH$_2$ × 2), 2.9~3.4 (NCH$_2$ × 5), 3.37 (OCH$_3$), 5.28 (CH) |
| 11 | 3400, 2930, 1655, 1520, 1460, 1360, 1190, 1150, 1090 | 1.2~2.0 (CH$_2$ × 8), 2.0~2.5 (CH$_2$ × 2), 2.9~3.4 (NCH$_2$ × 5), 3.37 (OCH$_2$), 5.29 (CH) |
| 12 | 3400, 2930, 1655, 1520, 1460, 1360, 1160, 1085 | 1.23 (CH$_3$), 1.3~2.0 (CH$_2$ × 6), 2.0~2.5 (CH$_2$ × 2), 2.9~3.4 (NCH$_2$ × 5), 3.64 (CH$_2$), 5.42 (CH) |
| 13 | 3380, 2925, 1655, 1520, 1455, 1360, 1156, 1080 | 0.92 (CH$_3$), 1.2~2.0 (CH$_2$ × 8), 2.0~2.5 (CH$_2$ × 2), 2.9~3.4 (NCH$_2$ × 5), 3.61 (CH$_2$), 5.41 (CH) |
| 14 | 3370, 2930, 1655, 1520, 1455, 1355, 1165, 1110, 1060 | 1.2~2.0 (CH$_2$ × 6), 2.0~2.5 (CH$_2$ × 2), 2.9~3.4 (NCH$_2$ × 5), 3.70 (CH$_2$ × 2), 5.45 (CH) |
| 15 | 3340, 2930, 1655, 1520, 1450, 1160, 1066, 1020, 740, 695 | 1.2~2.0 (CH$_2$ × 6), 2.0~2.5 (CH$_2$ × 2), 2.9~3.4 (NCH$_2$ × 5), 4.64 (CH$_2$), 5.51 (CH), 7.32 (C$_6$H$_5$) |
| 16 | 3350, 2930, 1660, 1520, 1460, 1355 | 1.4~2.4 (CH$_2$ × 6), 2.9~3.4 (NCH$_2$ × 5), 5.56 (CH), 6.01 (CH), 6.81 (CH) |
| 17 | 3400, 2925, 1660, 1530, 1460, 1360, 1165, 1115, 1080 | 1.4~2.5 (CH$_2$ × 7), 2.9~3.4 (NCH$_2$ × 5), 5.60 (CH), 6.02 (CH), 6.85 (CH) |
| 18 | 3400, 2940, 2850, 1660, 1530, 1460, 1360, 1225, 1115, 1080 | 1.2~2.5 (CH$_2$ × 8), 2.9~3.4 (NCH$_2$ × 5), 5.65 (CH), 6.04 (CH), 6.88 (CH) |
| 19 | 3400, 2940, 1665, 1520, 1455, 1350, 1195, 1095, 985 | 1.4~2.5 (CH$_2$ × 6), 2.9~3.4 (NCH$_2$ × 5), 3.4 (OCH$_3$), 5.39 (CH), 6.09 (CH), 6.90 (CH) |
| 20 | 3450, 2925, 1650, 1525, 1460, 1160, 1110, 1075 | 1.4~2.3 (CH$_2$ × 7), 2.38 (CH$_2$), 2.9~3.4 (NCH$_2$ × 5), 4.0 (CH), 5.52 (CH) |
| 21 | 3400, 2950, 1655, 1520, 1460, 1165, 1110, 1075 | 1.2~2.4 (CH$_2$ × 8), 2.41 (CH$_2$), 2.9~3.4 (NCH$_2$ × 5), 4.0 (CH), 5.58 (CH) |
| 22 | 3330, 2930, 1655, 1520, 1460, 1360, 1190, 1160, 1090, 1020 | 1.4~1.9 (CH$_2$ × 5), 2.19 (CH$_2$), 2.49 (CH$_2$), 2.9~3.4 (NCH$_2$ × 5), 3.41 (CH$_3$), 4.04 (CH), 5.35 (CH) |
| 23 | 3350, 2925, 1655, 1520, 1460, 1360, 1160, 1085, 1020 | 1.23 (CH$_3$), 1.4~1.9 (CH$_2$ × 5), 2.16 (CH$_2$), 2.46 (CH$_3$), 2.9~3.4 (NCH$_2$ × 5), 3.64 (CH$_2$), 4.02 (CH$_2$), 5.43 (CH) |
| 24 | 3380, 2925, 1655, 1520, 1455, 1370, 1155, 1080, 1020 | 0.92 (CH$_3$), 1.2~1.9 (CH$_2$ × 7), 2.09 (CH$_2$), 2.43 (CH$_2$), 2.9~3.4 (NCH$_2$ × 5), 3.61 (CH$_2$), 4.01 (CH), 5.41 (CH) |

TABLE 3-continued

| Compound No. | Infrared Absorption Spectrum (cm$^{-1}$) | Proton-NMR Spectrum (δ value) |
|---|---|---|
| 25 | 3375, 2930, 1655, 1520, 1450, 1165, 1115, 1060 | 1.4~1.9 (CH$_2$ × 5), 2.13 (CH$_2$), 2.45 (CH$_2$), 2.9~3.4 (NCH$_2$ × 5), 3.70 (CH$_2$ × 2), 4.02 (CH) 5.44 (CH) |
| 26 | 3330, 2930, 1655, 1520, 1445, 1360, 1160, 1065, 1020, 740, 695 | 1.4~1.9 (CH$_2$ × 5), 2.12 (CH$_2$), 2.46 (CH$_2$), 2.9~3.4 (NCH$_2$ × 5), 4.00 (CH), 4.64 (CH$_2$), 5.50 (CH), 7.32 (C$_6$H$_5$) |

TABLE 4

| Compound No. | Configuration Position 15 | Position 11 | Specific Rotation [α]$_D^{25}$ |
|---|---|---|---|
| 9 | | (±) | 0.0° (c 1, H$_2$O) |
| | | (−) | −30.4° (c 1, H$_2$O) |
| | | (+) | +29.5° (c 1, H$_2$O) |
| 22 | (S) | (±) | −1.0° (c 1, H$_2$O) |
| | | (−) | −27.3° (c 1, H$_2$O) |
| | | (+) | +25.5° (c 1, H$_2$O) |
| 23 | (S) | (±) | −0.2° (c 1, H$_2$O) |
| | | (−) | −25.0° (c 1, H$_2$O) |
| | | (+) | +24.2° (c 1, H$_2$O) |
| 24 | (S) | (±) | +0.5° (c 1, H$_2$O) |
| | | (−) | −22.9° (c 1, H$_2$O) |
| | | (+) | +23.5° (c 1, H$_2$O) |
| 25 | (S) | (±) | −2.1° (c 1, H$_2$O) |
| | | (−) | −18.7° (c 1, H$_2$O) |
| | | (+) | +15.8° (c 1, H$_2$O) |
| 26 | (S) | (±) | −3.1° (c 1, H$_2$O) |
| | | (−) | −24.3° (c 1, H$_2$O) |
| | | (+) | +21.0° (c 1, H$_2$O) |

TABLE 5

| Compound No. | Stability [Retention (%)] pH | | | | | | | | |
|---|---|---|---|---|---|---|---|---|---|
| | 2 | 3 | 4 | 5 | 6 | 7 | 8 | 9 | 10 |
| 9 | 69.3 | 89.3 | 100 | 100 | 100 | 100 | 100 | 97.5 | 97.9 |
| 13 | 72.4 | 90.1 | 100 | — | 100 | — | 100 | 98.0 | 96.0 |
| 14 | 71.8 | 90.6 | 100 | — | 100 | — | 100 | 97.5 | 97.3 |
| 15 | 76.5 | 91.4 | 100 | — | 100 | — | 100 | 99.0 | 96.2 |
| 22 (−) | 79.7 | — | 100 | 100 | 100 | 100 | 100 | 97.6 | 95.7 |
| (+) | 79.7 | — | 100 | 100 | 100 | 100 | 100 | 100 | 95.6 |
| 24 | 76.3 | — | 100 | 100 | 100 | 100 | 100 | 97.1 | 94.8 |
| 25 | 68.9 | — | 100 | 100 | 100 | 100 | 100 | 97.7 | 95.5 |
| 26 | 77.2 | — | 100 | 100 | 100 | 100 | 100 | 95.9 | 94.5 |
| (−)-sper-gualin | 88.1 | 88.0 | 87.8 | 82.5 | 46.5 | 12.6 | 6.1 | 0 | — |

(2) Biological properties.

All of the compounds of this invention possess a strong growth-inhibitory effect on cancer cells in vitro and a life-prolonging effect on mice bearing implanted cancer cells, as shown below.

I. Growth inhibitory activity to cancer cells in vitro

DBA/2 mice were implanted with 10$^5$ mouse leukemia L-1210 cells. The ascites collected aseptically from the mice after 4 days of feeding was washed three times with physiological saline to obtain L-1210 cells, which was then suspended in RPMI 1640 culture medium [G. E. Moore, Journal of the American Medical Association, Vol. 199, 519 (1967); H. J. Morton, In Vitro, Vol. 6, 89 (1970)] to which 10% fetal calf serum and 5 μM 2-mercaptoethanol had been added, and the resulting suspension was diluted to 5×10$^4$ L-1210 cells per 0.9 ml. A microplate carrying 0.9 ml of the cell suspension and 0.1 ml of the culture medium containing the sample being tested was kept in a carbon dioxide incubator at 37° C. After 48 hours of cultivation, the number of cells was measured by means of a Coulter Counter (Coulter Electronics, Inc., USA) to obtain the growth inhibition (%)=(1-T/C)×100=[1-(number of grown cells in medium containing sample/(number of grown cells in control medium)]×100. The 50% growth inhibitory concentration was calculated from the values of growth inhibition at varied sample concentrations. The results of tests on typical compounds of this invention for the growth inhibition of L-1210 cells were as shown in Table 6.

TABLE 6

| Compound No. | Growth inhibition (%), (1-T/C) × 100 Concentration of test compound, mcg/ml | | | | | | | | 50% inhibitory concentration (mcg/ml) |
|---|---|---|---|---|---|---|---|---|---|
| | 1.25 | 2.5 | 5 | 10 | 20 | 40 | 80 | 160 | |
| 1 | — | 52.2 | 89.3 | 101 | 100 | — | — | — | 2.4 |
| 2 | 9.6 | 30.5 | 46.9 | 69.5 | 77.6 | 79.6 | — | 5.0 | |
| 3 | 20.6 | 36.7 | 64.2 | 81.6 | 86.7 | — | — | — | 3.7 |
| 4 | 20.0 | 27.5 | 29.9 | 58.4 | 75.5 | 78.7 | — | — | 8.1 |
| 5 | — | 24.9 | 29.1 | 40.0 | 54.2 | 66.0 | 88.5 | 96.8 | 18 |
| 6 | 38.0 | 40.3 | 45.5 | 50.3 | 57.5 | — | — | — | 8.0 |
| 7 | 38.7 | 80.7 | 98.5 | 99.8 | 99.9 | 99.3 | — | — | 1.5 |
| 8 | — | — | 33.2 | 38.1 | 46.8 | 53.5 | 66.3 | 88.2 | 28 |
| 9 | — | — | 35.5 | 45.9 | 62.3 | 78.1 | 90.9 | 96.0 | 12 |
| 10 | — | — | 19.9 | 28.5 | 36.5 | 52.4 | 62.4 | 79.5 | 39 |
| 11 | — | — | 35.0 | 52.2 | 59.4 | 71.8 | 77.9 | — | 10 |
| 12 | — | 21.5 | 31.1 | 38.4 | 47.3 | 58.6 | 73.5 | — | 21 |
| 13 | 17.0 | 21.3 | 24.0 | 33.2 | 65.7 | 72.5 | — | — | 14 |
| 14 | — | — | 22.3 | 24.6 | 29.9 | 42.7 | 58.6 | — | 52 |
| 15 | 27.1 | 39.0 | 71.0 | 94.5 | 97.7 | 100 | — | — | 3.1 |

TABLE 6-continued

| Compound No. | Growth inhibition (%), (1-T/C) × 100 Concentration of test compound, mcg/ml | | | | | | | | 50% inhibitory concentration (mcg/ml) |
|---|---|---|---|---|---|---|---|---|---|
| | 1.25 | 2.5 | 5 | 10 | 20 | 40 | 80 | 160 | |
| 16 | — | 22.6 | 31.1 | 32.5 | 56.3 | — | — | — | 17 |
| 17 | 2.1 | 4.5 | 13.3 | 16.5 | 33.7 | 52.53 | — | — | 70 |
| 18 | — | — | 15.7 | 20.9 | 29.5 | 32.3 | 47.8 | — | 90 |
| 19 | 29.9 | 32.2 | 46.4 | 56.4 | 75.6 | 85.4 | 93.1 | — | 6.3 |
| 20 | 17.2 | 20.1 | 28.9 | 30.7 | 45.7 | — | — | — | 27 |
| 21 | 14.6 | 21.5 | 29.7 | 37.5 | 51.6 | 84.0 | 94.5 | — | 18 |
| 22 | — | 60.8 | 82.6 | 94.5 | 96.9 | 98.3 | — | — | 1.8 |
| 23 | — | 58.5 | 85.5 | 93.0 | 96.1 | 96.4 | — | — | 2.2 |
| 24 | — | 47.3 | 75.6 | 89.5 | 95.0 | 97.2 | — | — | 2.6 |
| 25 | — | 9.0 | 20.0 | 42.0 | 63.5 | 74.7 | — | — | 7.2 |
| 26 | — | 54.2 | 79.0 | 90.2 | 96.6 | 97.3 | — | — | 2.2 |

II. Therapeutic effect on implanted cancer in mice $BDF_1$ strain male mice (5 weeks old) were each inoculated intraperitoneally with $10^5$ mouse leukemia L-1210 cells and treated once a day by intraperitoneal injection with a test compound dissolved in physiological saline for 6 consecutive days beginning from the day of inoculation. The mice were then observed for 30 days to determine the rate of prolongation of survival period $=100\times T/C=100\times$(average survival days of treated group)/(average survival days of control group). The therapeutic effect of typical compounds of this invention on mouse leukemia L-1210 were as shown in Table 7.

TABLE 7

Treatment of Murine Leukemia L-1210

| Compound No. | Dosage (mg/kg/day) | Prolongation of survival period (%), T/C × 100 | Number of mice survived for 30 days |
|---|---|---|---|
| 4 | 50 | 0 | 0/4 |
| | 25 | 336 | 0/4 |
| | 12.5 | >357 | 2/4 |
| | 6.25 | >369 | 1/4 |
| | 3.13 | >364 | 2/4 |
| | 1.56 | >429 | 4/4 |
| | 0.78 | >429 | 4/4 |
| | 0.39 | >390 | 3/4 |
| | 0.20 | 197 | 0/4 |
| 5 | 50 | 0 | 0/4 |
| | 25 | 306 | 0/4 |
| | 12.5 | 181 | 0/4 |
| | 6.25 | 125 | 0/4 |
| | 3.13 | 118 | 0/4 |
| | 1.56 | 104 | 0/4 |
| 6 | 50 | 0 | 0/4 |
| | 25 | 0 | 0/4 |
| | 12.5 | >429 | 4/4 |
| | 6.25 | >429 | 4/4 |
| | 3.13 | >386 | 2/4 |
| | 1.56 | >393 | 3/4 |
| | 0.78 | >429 | 4/4 |
| | 0.39 | >383 | 2/4 |
| | 0.20 | >354 | 2/4 |
| 9 (±) | 50 | 0 | 0/4 |
| | 25 | 0 | 0/4 |
| | 12.5 | >429 | 4/4 |
| | 6.25 | >429 | 4/4 |
| | 3.13 | >429 | 4/4 |
| | 1.56 | >411 | 1/4 |
| | 0.78 | >300 | 2/4 |
| | 0.39 | 171 | 0/4 |
| | 0.20 | 114 | 0/4 |
| 9 (−) | 25 | 0 | 0/4 |
| | 12.5 | >390 | 2/4 |
| | 6.25 | >336 | 1/4 |
| | 3.13 | >411 | 3/4 |
| | 1.56 | >356 | 2/4 |
| | 0.78 | >370 | 2/4 |
| 10 | 50 | 0 | 0/4 |
| | 25 | 0 | 0/4 |
| | 12.5 | 129 | 0/4 |
| | 6.25 | 107 | 0/4 |
| | 3.13 | 100 | 0/4 |
| | 1.56 | 100 | 0/4 |
| 11 | 50 | 0 | 0/4 |
| | 25 | 0 | 0/4 |
| | 12.5 | >357 | 2/4 |
| | 6.25 | >393 | 3/4 |
| | 3.13 | >357 | 2/4 |
| | 1.56 | 200 | 0/4 |
| | 0.78 | 200 | 0/4 |
| | 0.39 | 143 | 0/4 |
| | 0.20 | 107 | 0/4 |
| 16 | 50 | 0 | 0/4 |
| | 25 | 236 | 0/4 |
| | 12.5 | >354 | 2/4 |
| | 6.25 | >350 | 2/4 |
| | 3.13 | >343 | 2/4 |
| | 1.56 | 233 | 0/4 |
| | 0.78 | 129 | 0/4 |
| 18 | 12.5 | 0 | 0/4 |
| | 6.25 | >350 | 2/4 |
| | 3.13 | >429 | 4/4 |
| | 1.56 | >429 | 3/4 |
| | 0.78 | 200 | 0/4 |
| | 0.39 | 157 | 0/4 |
| | 0.20 | 136 | 0/4 |
| | 0.10 | 129 | 0/4 |
| 19 | 25 | 0 | 0/4 |
| | 12.5 | >364 | 2/4 |
| | 6.25 | >429 | 3/4 |
| | 3.13 | >321 | 2/4 |
| | 1.56 | >350 | 2/4 |
| | 0.78 | 164 | 0/4 |
| | 0.39 | 107 | 0/4 |
| | 0.20 | 100 | 0/4 |
| 21 | 50 | 0 | 0/4 |
| | 25 | 229 | 0/4 |
| | 12.5 | 200 | 0/4 |
| | 6.25 | 164 | 0/4 |
| | 3.13 | 129 | 0/4 |
| | 1.56 | 114 | 0/4 |
| | 0.78 | 100 | 0/4 |
| | 0.39 | 100 | 0/4 |
| | 0.20 | 100 | 0/4 |
| 22 (S) (±) | 50 | 7 | 0/8 |
| | 25 | >414 | 6/8 |
| | 12.5 | >380 | 5/8 |
| | 6.25 | >332 | 4/8 |
| | 3.13 | 163 | 0/8 |
| | 1.56 | 117 | 0/8 |

Note: values for compound 9(−) include additionally 0.39 >342, 0.20 127, 0.10 110 as listed at top of continued table.

TABLE 7-continued
Treatment of Murine Leukemia L-1210

| Compound No. | Dosage (mg/kg/day) | Prolongation of survival period (%), T/C × 100 | Number of mice survived for 30 days |
|---|---|---|---|
| 22 | 25 | >423 | 5/5 |
| (S) | 12.5 | >408 | 4/5 |
| (−) | 6.25 | >400 | 4/5 |
|  | 3.13 | >290 | 1/5 |
|  | 1.56 | 177 | 0/5 |
| 23 | 25 | 200 | 0/4 |
|  | 12.5 | 129 | 0/4 |
|  | 6.25 | 119 | 0/4 |
|  | 3.13 | 104 | 0/4 |
| 25 | 50 | >429 | 4/4 |
|  | 25 | 229 | 0/4 |
|  | 12.5 | 193 | 0/4 |
|  | 6.25 | 107 | 0/4 |

III. Toxicity

All of the compounds of this invention exhibit a comparatively low toxicity and are characterized by a low cumulative toxicity on continued administration. In Table 8 median lethal doses (LD$_{50}$) of typical compounds of this invention are shown, measured in mice upon single intraperitoneal administration, as well as maximum tolerated doses in terms of total dose when a fixed amount per unit body weight was administered intraperitoneally to mice once a day for 6 consecutive days.

TABLE 8
Acute and Cumulative Toxicity in Mice

| Compound No. | LD$_{50}$* (mg/kg) | Maximum Tolerated Dose** (mg/kg) |
|---|---|---|
| 1 | 50< | 300< |
| 2 | 50< | 300< |
| 3 | 50< | 300< |
| 4 | 25–50 | 150< |
| 5 | 25–50 | 150< |
| 6 | 12.5–25 | 75< |
| 8 | 25–50 | 150< |
| 9 | 12.5–25 | 75< |
| 10 | 12.5–25 | 75< |
| 11 | 12.5–25 | 75< |
| 12 | 12.5–25 | 75< |
| 14 | 25–50 | 150< |
| 15 | 12.5–25 | 75< |
| 16 | 25–50 | 150< |
| 17 | 12.5–25 | 75< |
| 18 | 6.25–12.5 | 37.5< |
| 19 | 12.5–25 | 75< |
| 20 | 50< | 300< |
| 21 | 25–50 | 150< |
| 22 | 25–50 | 150< |
| 23 | 25< | 150< |
| 24 | 50< | 300< |
| 25 | 50< | 300< |
| 26 | 12.5–25 | 75< |

*Median lethal dose on single administration.
**Maximum value of the total dose not causing death when a fixed amount per unit body weight is administered to mice once a day for 6 consecutive days.

As is apparent from the foregoing description, the compounds of this invention represented by the formula I have antitumor activity in animals. They exhibit an excellent growth-inhibitory activity against mouse leukemia L-1210 cells. In these compounds, R is a hydrogen atom, an alkyl group of 1 to 4 carbon atoms which may have a hydroxyl group as substituent, or a benzyl group, and n is an integer of from 1 to 6, provided that when Y is

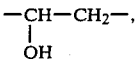

R represents the groups other than the hydrogen atom. Further, an excellent therapeutic effect upon the mice bearing implanted cancer was manifested by those compounds in which R is a hydrogen atom or an alkyl group of one or two, preferably one, carbon atom, which may have a hydroxyl group as substituents, and n is 4 or 6. Of these compounds, those in which R is a methyl group (an alkyl group of one carbon atom) are excellent also in chemical stability, compound Nos. 9, 19 and 22 being most desirable.

The invention includes the method for inhibiting tumor growth with a compound Formula I. For this purpose, the compound is administered systemically, preferably by parenteral injection and on a repetitive dosage regimen, to a tumor-bearing mammal in a non-toxic tumor-inhibitory effective amount.

The process for the synthesis of the compounds of this invention is described below.

Although it can be effected in organic solvents, the condensation of an ω-guanidino fatty acid amide of the formula II and a dihydroxyethanamide of the formula III according to this invention is generally carried out in the presence of small amounts of water, because of the solubility of both compounds which are generally treated in the form of acid addition salts.

When organic solvents are to be used, acetone and dimethylformamide are suitable, but the condensation is generally conducted in the presence of small amounts of water without using organic solvents. The amount of water to be used should be the least possible for dissolving both compounds. In practice, it is used in an amount in the range of from 2 to 60, preferably from 4 to 40, moles for 1 mole of the guanidino fatty acid amide of the formula II. Since these compounds of formulas II and III are usually treated in the form of acid addition salt, it is not necessary to add an acid. However, in view of the yield of condensate, it is preferable to use an acid catalyst. Suitable acid catalysts include inorganic acids such as hydrochloric acid, sulfuric acid, phosphoric acid and boric acid and organic acids such as acetic acid, citric acid, tartaric acid, succinic acid, glutaric acid and adipic acid. A dicarboxylic acid such as glutaric acid is preferred. The amount of an acid to be used is 0 to 10, preferably 0.5 to 4, moles per mole of guanidino fatty acid amide of formula II. The reaction temperature is 0° to 100° C., usually from room temperature to 80° C., preferably 40° to 70° C. The reaction time varies with the reaction temperature. A reaction time of 1 to 2 days is preferred for increasing the yield.

Although the ratio of guanidino fatty acid amide of formula II to dihydroxyethanamide of formula III is not specifically limited, it is general practice to use 0.5 to 4, preferably 0.8 to 1.5, moles of the latter for 1 mole of the former. The resulting compound is an N-[4-(3-aminopropyl)aminobutyl]-2-(ω-guanidinofatty-acid-amido)-2-hydroxyethanamide represented by the general formula $$\underset{\underset{NH}{\|}}{H_2NCNH(CH_2)_n}-Y-\overset{13\ 12\ 11\ 10\ 9\ 8\ 7\ 6\ 5\ 4\ 3\ 2\ 1}{CONH\underset{\underset{OH}{|}}{CH}CONHCH_2CH_2CH_2CH_2NHCH_2CH_2CH_2NH_2} \qquad Ia$$

wherein Y and n are as defined above, which is the compound of formula I in which R is a hydrogen atom.

The compounds of formula I in which R is the groups other than the hydrogen atom are obtained by alkylating the hydroxyl group at the position 11 of the compound of formula Ia with the aforesaid aliphatic alcohol, diazoparaffin or benzyl alcohol. The compound obtained by the above condensation or spergualin obtained from the microbial culture broth can be used for the compound of formula Ia. The compound obtained by the alkylation is an N-[4-(3-aminopropyl)aminobutyl]-2-(ω-guanidinofatty-acid-amido)-2-alkoxyethanamide represented by the general formula $$\underset{\underset{NH}{\|}}{H_2NCNH(CH_2)_n}-Y-CONH\underset{\underset{OR'}{|}}{CH}CONH(CH_2)_4NH(CH_2)_3NH_2 \qquad Ib$$

wherein Y and n are as defined above and R' represents an alkyl group of 1 to 4 carbon atoms, which may have a hydroxyl group as substituent, or benzyl group. The alkylation is carried out in the following manner.

The reaction between an N-[4-(3-aminopropyl)aminobutyl]-2-(ω-guanidinofatty-acid amido)-2-hydroxyethanamide of formula Ia and the alcohol is carried out generally in the presence of an acid catalyst. Before the reaction the guanidino and amino groups in the hydroxyethanamide of formula Ia are not necessarily protected, but can be protected. The alcohol is represented by the formula $$R'-OH \qquad IV$$

wherein R' is an alkyl group of 1 to 4 carbon atoms which may have a hydroxyl group as substituent, or a benzyl group. Such alcohols include lower alcohols such as methanol, ethanol, propanol and butanol, glycols such as ethylene glycol and propylene glycol, and benzyl alcohol. The reaction is carried out preferably in the alcohol of the above formula IV, though an inert solvent may be used. Suitable acid catalysts include inorganic acids such as hydrochloric and sulfuric acid, organic acids such as acetic acid and p-toluenesulfonic acid, and cationic exchange resins. The reaction temperature is in the range of from 0° to 100° C., generally from room temperature to 80° C., room temperature being most preferred. The reaction time varies with the reaction temperature and ranges from 1 hour to 10 days, preferably from 1 to 2 days.

When the solubility of a hydroxyethanamide of the formula Ia in an alcohol of the formula IV is low, the protection of amino and imino groups of the hydroxyethanamide with protective groups is advantageous for increasing the yield. Suitable protective groups can be selected by referring to the literature (J. F. W. Mcomie, Ed., "Protective Groups in Organic Chemistry", Plenum Press, NY, 1973). Those protective groups for amino group which are generally used in the peptide synthesis are useful. Examples are monovalent protective groups such as benzyloxycarbonyl, p-methoxybenzyloxycarbonyl, p-nitrobenzyloxycarbonyl, tert-butoxycarbonyl, trichloroethoxycarbonyl and isobornyloxycarbonyl and divalent protective groups such as phthaloyl and succinyl. Of these groups, preferred are aralkyloxycarbonyl groups such as benzyloxycarbonyl and p-methoxybenzyloxycarbonyl groups because of the ease of introduction and removal. The introduction of these protective groups is effected by known procedures and advantageously by the method of active ester. In this procedure, the guanidino group in the compound of formula Ia remains unchanged.

The alkylation of the hydroxyl group at the position 11 of the hydroxyethanamide of formula Ia by the reaction with a diazoparaffin is performed in the following way.

Generally, at first the amino and imino groups of the hydroxyethanamide of formula Ia are protected with the above-noted protective group and the resulting compound is subjected to the reaction with a diazoparaffin in an inert organic solvent such as methylene chloride or tetrahydrofuran at a temperature of −20° to 20° C., usually −10° to 10° C., preferably −3° to 3° C. for 1 to 15, usually 2 to 8, hours to effect alkylation. The reaction does not necessarily require a catalyst, but it is accelerated in the presence of a Lewis acid catalyst such as boron trifluoride, aluminum chloride, hydrofluoboric acid or selenium dioxide. As examples of diazoparaffins of 1 to 4 carbon atoms, mention may be made of diazomethane, diazoethane, diazopropane and diazobutane. These diazoparaffins may be synthesized from corresponding N-nitrosoalkylurea, N-nitrosoalkylurethane, N-nitrosoalkylsulfonamide and N-nitrosoalkyl-N'-nitroguanidine by the known procedures [e.g. "Organic Synthesis" (John Wiley and Sons, Inc.), II, 165 (1943); III, 119 (1955); Journal of Organic Chemistry, 13, 763 (1948); "Organic Synthesis", IV, 250 (1963); Chemische Berichte, 94, 2547 (1961); Canadian Journal of Research, 28B, 683 (1950); "Organic Synthesis", III, 244 (1955); Journal of Chemical Society, 1935, 286].

The alkylation with a diazoparaffin enables the hydroxyl group at the position 11 to become alkylated without change in the configuration at position 11 of the formula Ia. For instance, a (−) hydroxyethanamide of formula Ia is converted to the corresponding (−) alkoxyethanamide or an epimeric mixture (±) with respect to position 11 is obtained from the (+) hydroxyethanamide or (±) hydroxyethanamide, respectively.

The hydroxyethanamide compound of formula Ia will have hydroxyl groups at both positions 11 and 15 when Y is $$-\underset{\underset{OH}{|}}{CH}-CH_2-.$$

In this case, owing to the difference in reactivity between two hydroxyl groups, it is possible to alkylate selectively the hydroxyl group at position 11.

The protective groups for the amino and imino groups of the alkylated product can be removed in an ordinary way, leaving behind an alkoxyethanamide of formula Ib. For instance, when the protective group is an aralkyloxycarbonyl group, it can be removed by the ordinary catalytic hydrogenation at atmospheric pressure. The reaction is carried out in a suitable solvent such as methanol, ethanol, dioxane or a mixture thereof in the presence of palladium or platinum as catalyst. The reaction is accelerated by the addition of an acid such as hydrochloric acid or acetic acid.

When Y is $$-\underset{\underset{OH}{|}}{CH}-CH_2,$$

the 2-substituted ethanamide of the formula I is N-[4-(3-aminopropyl)aminobutyl]-2-(ω-guanidino-β-hydroxyfatty-acid-amido)-2-substituted-ethanamide represented by the general formula $$\overset{15\ 14\ 13\ 12\ 11\ 10\ 9\ 8-5\ \ \ 4\ 3-1}{H_2N\underset{\underset{NH}{\|}}{C}NH(CH_2)_n\underset{\underset{OH}{|}}{C}HCH_2CONHCHCONH(CH_2)_4NH(CH_2)_3NH_2} \quad \text{Ic}$$
$$\phantom{H_2NCNH(CH_2)_nCHCH_2CONH}\underset{\underset{OR}{|}}{\phantom{C}}$$

wherein R and n are as defined above, provided that when n is 4, R represents the groups other than the hydrogen atom. When the configuration at the position 15 of this compound is either (S) or (R) and the compound is an epimeric mixture with respect to the position 11, the compound can be separated into both epimers [(+)-form and (−)-form] by means of chromatography. For this purpose, high-performance liquid chromatography (HPLC) is suitable. A desirable result is obtained by using, for example, Nucleosil® C18 (M. Nagel Co.) as column packing material and a mixture of acetonitrile-sodium pentanesulfonate-phosphate buffer as eluant.

As described above, alkylation of the hydroxyl group at position 11 with a diazoparaffin or separation by HPLC yields an optically active N-[4-(3-aminopropyl)aminobutyl]-2-(ω-guanidino-β-hydroxyfatty-acid-amido]-2-alkoxyethanamide represented by the general formula $$\overset{15\ 14\ 13\ 12\ 11}{H_2N\underset{\underset{NH}{\|}}{C}NH(CH_2)_n\underset{\underset{OH}{|}}{C}HCH_2CONHCHCONH(CH_2)_4NH(CH_2)_3NH_2} \quad \text{Id}$$
$$\phantom{H_2NCNH(CH_2)_nCHCH_2CONH}\underset{\underset{OR'}{|}}{\phantom{C}}$$

wherein R' and n are as defined above. When the hydroxyl group at position 15 of this compound is removed by dehydration, there will be formed an optically active N-[4-(3-aminopropyl)aminobutyl]-2-[ω-guanidino-(α,β-unsaturated)fatty-acid-amido]-2-alkoxyethanamide represented by the general formula $$H_2N\underset{\underset{NH}{\|}}{C}NH(CH_2)_nCH=CHCONH\underset{\underset{OR'}{|}}{C}HCONH(CH_2)_4NH(CH_2)_3NH_2 \quad \text{Ie}$$

wherein R' and n are as defined above, which on hydrogenation yields an optically active N-[4-(3-aminopropyl)aminobutyl]-2-[ω-guanidino(saturated)fatty-acid-amido]-2-alkoxyethanamide represented by the general formula $$H_2N\underset{\underset{NH}{\|}}{C}NHCH(CH_2)_nCH_2CH_2CONH\underset{\underset{OR'}{|}}{C}HCONH(CH_2)_4NH(CH_2)_3NH_2 \quad \text{If}$$

wherein R' and n are as defined above.

The compound of formula Ie is obtained by protecting the amino and imino groups of the compound of formula Id with the aforesaid protective groups, subjecting the resulting compound to dehydration treatment, and removing the protective groups. The dehydration can be effected, for example, by a known method in which dicyclohexylcarbodiimide is allowed to react in the presence of a copper (I or II) chloride [Journal of the American Chemical Society, 90, 3245 (1965)]. This method is preferable because it is carried out under mild neutral conditions. An excess of dicyclohexylcarbodiimide curtails the reaction time. In view of the solubility of starting materials, N,N-dimethylformamide is an example of suitable solvent. The reaction temperature is usually from room temperature to 100° C. The reaction time varies from several hours to several days depending upon the reaction temperature.

The compound of formula If is advantageously obtained from the compound of formula Ie by the reduction of double bond. The reduction of double bond is effected by customary methods such as, for example, catalytic reduction. If the amino or imino protective group is an aralkyloxycarbonyl group, the reduction of double bond and the removal of protective groups are simultaneously achieved by the catalytic reduction.

When R' of the alkoxyethanamide compound of formula Ib is a benzyl group, the benzyl group is removed by the catalytic reduction and the compound is converted to the hydroxyethanamide compound of formula Ia while retaining the configuration at position 11 unchanged. In this case, the catalytic reduction for the removal of a protecting aralkyloxycarbonyl group proceeds at a low rate under atmospheric pressure, whereas a satisfactory result is obtained with reduced reaction time by carrying out the reaction in aqueous acetic acid solution under a higher pressure of several to several tens atmospheres.

The ω-guanidino fatty acid amide represented by the formula $$H_2N\underset{\underset{NH}{\|}}{C}NH(CH_2)_n-Y-CONH_2 \quad \text{II}$$

wherein Y and n are as defined above, which is a starting material for the synthesis of the compound of formula Ia, is synthesized as described below.

(a) Synthesis of a compound of formula II in which Y is —CH$_2$CH$_2$—:

This compound is an ω-guanidino saturated fatty acid amide represented by the general formula $$H_2N\underset{\underset{NH}{\|}}{C}NH(CH_2)_nCH_2CH_2CONH_2 \quad \text{IIa}$$

wherein n is as defined above. These ω-guanidino saturated fatty acid amides are known compounds and can be synthesized from commercial raw materials by known reactions. For instance, the compound is obtained by protecting the amino group of an ω-amino fatty acid of the formula $$H_2N(CH_2)_nCH_2CH_2COOH \quad \text{V}$$

where n is as defined above, then esterifying the carboxyl group, treating the resulting ester with ammonia to convert into an amide, removing the amino protective group and converting the amino group to a guanidino group.

The compound of formula IIa can also be prepared by oxidizing a diamine to a corresponding nitrile compound represented by the formula $$H_2N(CH_2)_nCH_2CH_2CN \qquad VI$$

wherein n is as defined above, then hydrolyzing the nitrile group to form an amide compound and converting the amino group to a guanidino group. Examples of particular ω-guanidino saturated fatty acid amides of formula IIa include 4-guanidinobutanamide, 5-guanidinopentanamide, 6-guanidinohexanamide, 7-guanidinoheptanamide, 8-guanidinooctanamide, 9-guanidinononanamide, 10-guanidinodecanamide and 11-guanidinoundecanamide.

(b) Synthesis of a compound of formula II in which Y is $$-\underset{\underset{OH}{|}}{CH}-CH_2-:$$

This compound is an ω-guanidino-β-hydroxy fatty acid amide represented by the general formula $$H_2N\underset{\underset{NH}{\|}}{C}NH(CH_2)_n\underset{\underset{OH}{|}}{C}HCH_2CONH_2 \qquad IIb$$

wherein n is as defined above, and is synthesized by known reactions in various ways. For instance, it is synthesized by protecting the amino group of an ω-amino fatty acid represented by the formula $$H_2N(CH_2)_nCOOH \qquad VII$$

wherein n is as defined above, then extending the carbon chain by two carbon atoms, converting the resulting compound to a β-hydroxy fatty acid amide through a series of reactions generally used in preparing a β-hydroxycarboxylic acid derivative, then removing the protective group to regenerate the amino group, and converting the amino group into guanidino group. The procedure is further described below in detail with reference to an example.

For instance, the ω-guanidino-β-hydroxy fatty acid amide of formula IIb may be synthesized by protecting the amino group of an ω-amino fatty acid of formula VII with an amino-protective group such as benzyloxycarbonyl group, converting the carboxylic acid into a reactive derivative such as an acid imidazolide, condensing the reactive derivative with magnesium enolate of monoethyl malonate of the formula

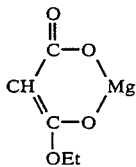

VIII

[Buletin de la Societe Chimique de France, 945 (1964)] to yield a β-keto ester of the formula $$X'-NH(CH_2)_nCOCH_2COOEt \qquad IX$$

wherein X' represents an amino-protective group and n is as defined above, reducing the ketone carbonyl group to form a β-hydroxy ester, treating the ester with ammonia to form an amide, removing the amino-protective group, and converting the regenerated amino group into guanidino group. As examples of ω-guanidino-β-hydroxy fatty acid amides thus prepared, mention may be made of 4-guanidino-3-hydroxybutanamide, 5-guanidino-3-hydroxypentanamide, 6-guanidino-3-hydroxyhexanamide, 7-guanidino-3-hydroxyheptanamide, 8-guanidino-3-hydroxyoctanamide and 9-guanidino-3-hydroxynonanamide.

(S)-7-guanidino-3-hydroxyheptanamide may be obtained by hydrolyzing with an acid or alkali the antibiotic substance BMG 162-aF2 (spergualin) represented by the formula $$\overset{(S)}{H_2N\underset{\underset{NH}{\|}}{C}NH(CH_2)_4\underset{\underset{OH}{|}}{C}HCH_2CONHCHCONH(CH_2)_4NH(CH_2)_3NH_2}$$
$$\qquad\qquad\qquad\qquad\qquad\underset{OH}{|}$$

which is isolated from the culture filtrate of a microorganism of the genus Bacillus, such as, for example, Bacillus BMG 162-aF2 (FERM-P 5230; ATCC 31932). It may also be synthesized, as described in the Journal of Antibiotics, Vol. 34, 1625 (1981) and in U.S. patent application Ser. No. 375,950, by forming (S)-3,7-diaminoheptanoic acid from L-lysine by Arndt-Eistert reaction [Journal of Organic Chemistry, Vol. 17, 347 (1952)], then deaminating the β-amino group with a nitrous acid, converting the carboxyl group into an amide group and further converting the amino group into guanidino group.

(c) Synthesis of a compound of formula II in which Y is —CH=CH—:

This compound is an ω-guanidino-α,β-unsaturated fatty acid amide represented by the formula $$H_2N\underset{\underset{NH}{\|}}{C}NH(CH_2)_nCH=CHCONH_2 \qquad IIc$$

wherein n is as defined above. These compounds are advantageously synthesized by the dehydration of ω-guanidino-β-hydroxy fatty acid amides of formula IIb, the preparation of which is described above. Although the dehydration can be effected by the methods customarily used in dehydrating a β-hydroxy fatty acid amide, it is preferable to carry out the reaction under mild neutral conditions. One of the suitable ways is to effect dehydration by the action of dicyclohexylcarbodiimide in the presence of copper(II) chloride [Journal of the American Chemical Society, 90, 3245 (1968)]. Since the compound of formula IIb is generally treated in the form of acid addition salt, a preferable solvent is N,N-dimethylformamide because of the solubility of the acid addition salt. The reaction temperature is generally from room temperature to 100° C. The reaction time generally ranges from several hours to several days depending upon the reaction temperature. The reaction time can be reduced by using the dicyclohexylcarbodiimide in excess. Examples of ω-guanidino-α,β-unsaturated fatty acid amides thus prepared include 4-guanidino-2-butenamide, 5-guanidino-2-pentenamide, 6-guanidino-2-hexenamide, 7-guanidino-2-heptenamide, 8-guanidino-2-octenamide and 9-guanidino-2-nonenamide.

The reduction of the double bond in the ω-guanidino-α,β-unsaturated fatty acid amide of formula IIc either catalytically in a customary manner or by use of sodium borohydride in the presence of a transition metal compound such as nickel chloride or cobalt chloride [Chemical and Pharmaceutical Bulletin, 19, 817 (1971)] gives an ω-guanidino saturated fatty acid amide of formula IIa.

N-[4-(3-Aminopropyl)aminobutyl]-2,2-dihydroxyethanamide of the formula

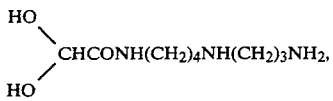  III which is a starting material for the synthesis of the compound of formula Ia is synthesized in the following way, as reported in detail in the Journal of Antibiotics, Vol. 34, 1625 (1981) and in U.S. patent application Ser. No. 375,916.

The free amino group of the compound represented by the formula

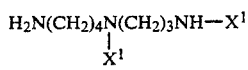  X wherein $X^1$ represents an amino-protective group, is acylated with a dialkylacetal of glyoxylic acid represented by the formula

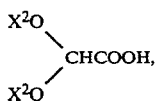  XI wherein $X^2$ represents an alkyl group of 1 to 5 carbon atoms, or with a reactive derivative of the carboxyl group, and then the amino-protective group $X^1$ and alkyl groups $X^2$ are removed, yielding the compound of formula III.

The compound of formula III may also be obtained in a high yield by the hydrolysis of aforementioned antibiotic substance BMG 162-aF2 (spergualin).

The invention is illustrated below with reference to Reference Examples and Examples.

REFERENCE EXAMPLE 1

Synthesis of (S)-7-guanidino-3-hydroxyheptanamide (a) Synthesis of (S)-3,7-diaminoheptanoic acid To a solution of 15 g (82.15 mmoles) of L-lysine hydrochloride in 150 ml of water, were added 8.7 g (82.15 mmoles) of sodium carbonate and 43.2 g (200 moles) of N-ethoxycarbonylphthalimide. The mixture was stirred for 20 hours at room temperature. The reaction mixture was washed with 50 ml of ethyl acetate. The aqueous layer was adjusted to pH 3.0 with 6N hydrochloric acid and extracted three times with 100 ml of toluene. The extract was washed twice with 100 ml of water (pH 2.0), dried over anhydrous sodium sulfate and evaporated to dryness under reduced pressure to yield 27.95 g (84% yield) of a white powder of di-N-phthaloyl-L-lysine; decomposition point, 71°–72° C.; $[\alpha]_D^{22}-32°$ (c 1, methanol).

To 27.0 g (66.4 mmoles) of di-N-phthaloyl-L-lysine, was added 40 ml of oxalyl chloride. The mixture was heated in an oil bath at 90° C., then admixed with 40 ml of 1,2-dimethoxyethane, and heated under reflux for 2 hours. The reaction mixture was evaporated to dryness, dissolved again in 20 ml of 1,2-dimethoxyethane, and added dropwise to 500 ml of an ether solution containing 330 mmoles of diazomethane while cooling in ice water. The mixture was then stirred for one hour. The reaction mixture was evaporated to dryness and dissolved in 250 ml of anhydrous methanol. To the solution was added 50 ml of a triethylamine solution containing 3.4 g (14.8 mmoles) of silver benzoate. The mixture was stirred at room temperature for 15 hours. The precipitate was collected by filtration, dissolved in 100 ml of chloroform, filtered from insolubles and evaporated to dryness to yield 15.3 g (53% yield) of (S)-3,7-diphthaloylaminoheptanoic acid methyl ester. Decomposition point, 118°–119° C.; $[\alpha]_D^{22}-3°$ (c 2, chloroform).

To 15.0 g (34.5 mmoles) of (S)-3,7-diphthaloylaminoheptanoic acid methyl ester were added 100 ml of 1M ethanolic hydrazine hydrate and 100 ml of 95% ethanol. The mixture was heated (oil bath temperature: 90° C.) under reflux for one hour. The reaction mixture was evaporated to dryness, dissolved in 250 ml of 5% hydrochloric acid, heated at 80° C. for one hour, adjusted to pH 7.1 with 17% aqueous ammonia and passed through a column (27 mm inner diameter) packed with 300 ml of Amberlite ® CG-50 (70% NH4-type). The column was washed successively with 900 ml of water and 900 ml of 0.2M aqueous ammonia and eluted with 0.5M aqueous ammonia. The ninhydrin-positive fractions were collected and evaporated to dryness to yield 3.15 g (57% yield) of (S)-3,7-diaminoheptanoic acid ($C_7H_{16}N_2O_2 \cdot \frac{1}{4}H_2CO_3$) in colorless syrup form; $[\alpha]_D^{21}+2.9°$ (c 1, water).

(b) Synthesis of (S)-7-guanidino-3-hydroxyheptanamide

To 30 ml of a pyridine-water-triethylamine (10:10:1) mixture containing 3.1 g (19.3 mmoles) of the (S)-3,7-diaminoheptanoic acid obtained in (a) above was added slowly 4.81 g (19.3 mmoles) of N-benzyloxycarbonyloxysuccinimide. The mixture was stirred for 5 hours at room temperature. The reaction mixture was evaporated to dryness, then dissolved in 30 ml of water, adjusted to pH 6.4 with 6N hydrochloric acid and passed through a 100-ml column (16 mm inner diameter) packed with Amberlite ® CG-50 (80% NH4-type). The column was developed with 300 ml of water. The collected effluent was further passed through a column (16 mm inner diameter) packed with 100 ml of Dowex ® 50W-X4 (H-type). The column was washed successively with each 300 ml of water and 0.2M aqueous ammonia and eluted with 0.5M aqueous ammonia (10 ml fraction size). The fraction Nos. 16 to 33 were combined and evaporated to dryness to yield 2.73 g (48% yield) of a white powder of (S)-3-amino-7-benzyloxycarbonylaminoheptanoic acid ($C_{15}H_{22}N_2O_4 \cdot H_2O$); decomposition point, 143°–147° C.; $[\alpha]_D^{22}+14°$ (c 1, methanol). The Amberlite ® CG-50 column was eluted with 0.5N aqueous ammonia to recover 746 mg (24% recovery) of (S)-3,7-diaminoheptanoic acid.

To a solution of 2.7 g (9.17 mmoles) of (S)-3-amino-7-benzyloxycarbonylaminoheptanoic acid in 33% aqueous acetic acid, while being cooled in ice, was added dropwise over a period of one hour a solution of 1.9 g (27.51 mmoles) of sodium nitrite in 10 ml of water. The mixture was further stirred for one hour and left standing at 5° C. for 24 hours. After addition of 50 ml of water, the reaction mixture was extracted twice with 50 ml of ethyl acetate. The organic layer was dried over anhydrous sodium sulfate and evaporated to dryness to yield 2.16 g of a crude powder. By using column (28 mm inner diameter) chromatography with 200 g of silica gel (Wakogel ® C-200), the above crude powder was developed with a chloroform-methanol-concentrated aqueous ammonia (30:10:1 by volume) mixture (20 ml fraction size). The fraction Nos. 51 to 60 were combined and evaporated to dryness to yield 460 mg (17% yield) of a white powder of (S)-7-benzyloxycarbonylamino-3-hydroxyheptanoic acid; decomposition point, 115°–117° C.; $[\alpha]_D^{23}+3$ (c 2, methanol).

To a solution of 450 mg (1.52 mmoles) of (S)-7-benzyloxycarbonylamino-3-hydroxyheptanoic acid in 1,2-dimethoxyethane, while being cooled in ice, was added dropwise 7 ml (4.56 mmoles) of a solution of diazomethane in ether. The mixture was stirred for 30 minutes. The reaction mixture was evaporated to dryness to yield 461 mg (98% yield) of (S)-7-benzyloxycarbonylamino-3-hydroxyheptanoic acid methyl ester; $[\alpha]_D^{21}+1°$.

A solution of 450 mg (1.45 mmoles) of (S)-7-benzyloxycarbonylamino-3-hydroxyheptanoic acid methyl ester in 50 ml of anhydrous methanol, while being cooled at −10° C., was saturated with gaseous ammonia and left standing in a sealed tube at room temperature for 3 days. The reaction mixture was evaporated to dryness and subjected to chromatography by using a column (20 mm inner diameter) containing 50 g of silica gel (Wakogel ® C-200) and developing with chloroform-methanol (100:1 by volume). Fraction Nos. 82 to 106 (each 10 ml in volume) were combined and evaporated to dryness to yield 371 mg (87% yield) of a white powder of (S)-7-benzyloxycarbonylamino-3-hydroxyheptanamide; decomposition point, 126°–127° C.; $[\alpha]_D^{22}-3°$ (c 5, methanol).

Into a mixture of 10 ml of 90% aqueous methanol and 0.01 ml of acetic acid was dissolved 350 mg (1.19 mmoles) of (S)-7-benzyloxycarbonylamino-3-hydroxyheptanamide. After adding 50 mg of 5% palladium-carbon, the mixture was stirred under a hydrogen stream at room temperature for 3 hours. After removal of the catalyst by filtration, the filtrate was evaporated to dryness, dissolved again in a small volume of water and passed through a column (12 mm inner diameter) containing 30 ml of Dowex ® 50W-X4 (H-type). The column was washed with 90 ml of water and eluted with 0.5M aqueous ammonia (3 ml in fraction size). The fraction Nos. 28 to 34 were combined and evaporated to dryness to yield 201 mg (96% yield) of (S)-7-amino-3-hydroxyheptanamide; $[\alpha]_D^{22}-2°$ (c 2, water).

To a solution of 190 mg (1.08 mmoles) of (S)-7-amino-3-hydroxyheptanamide in 3 ml of water was added 0.54 ml of 2N aqueous sodium hydroxide solution. To the resulting solution, while being cooled in ice, was added dropwise over a period of 30 minutes 1 ml of a methanol solution containing 129 mg (1.08 mmoles) of 2-methyl-1-nitrosourea. The mixture was further stirred for 5 hours, then adjusted to pH 6.0 with 6N hydrochloric acid, evaporated to dryness and purified by chromatography using a column (15 mm inner diameter) containing 30 g of silica gel (Wakogel ® C-200) and developing with a mixture of chloroform, methanol and concentrated aqueous ammonia (60:10:1 by volume). Fractions Nos. 67 to 90 (6 ml in fraction size) were combined and evaporated to dryness to yield 187 mg (70% yield) of a white powder of (S)-7-nitroguanidino-3-hydroxyheptanamide; decomposition point, 148°–149° C.; $[\alpha]_D^{22}-2°$ (c 2, methanol).

Into a mixture of 15 ml of water, 15 ml of methanol and 7.5 ml of acetic acid was dissolved 170 mg (0.69 mmoles) of (S)-7-nitroguanidino-3-hydroxyheptanamide. After adding 50 mg of 5% palladium-carbon, the mixture was stirred under a hydrogen stream for one hour at room temperature. After removing the catalyst by filtration, the filtrate was evaporated to dryness to obtain 165 mg of a crude powder. The crude powder was dissolved in 10 ml of water, passed through a column (12 mm inner diameter) packed with 20 ml of CM-Sephadex ® C-25 (Na-type), and eluted with 0.5M aqueous sodium chloride solution (2 ml in fraction size). Fraction Nos. 18 to 25 were combined, evaporated to dryness and extracted three times with 10 ml of methanol. The methanol solutions were combined, passed through a column (20 mm inner diameter) packed with 100 ml of Sephadex ® LH-20, and eluted with methanol (1 ml in fraction size). Fraction Nos. 28 to 46 were combined and evaporated to dryness to yield 149 mg (91% yield) of a white powder of (S)-7-guanidino-3-hydroxyheptanamide hydrochloride ($C_8H_{18}N_4O_2$·HCl); $[\alpha]_D^{22}-2°$ (c 2, water).

REFERENCE EXAMPLE 2

Synthesis of 7-guanidino-2-heptenamide

To a solution of 955 mg (4 mmoles) of (S)-7-guanidino-3-hydroxyheptanamide hydrochloride in 20 ml of anhydrous N,N-dimethylformamide were added 2.48 g (12 mmoles) of dicyclohexylcarbodiimide and 40 mg of copper(II) chloride. The mixture was stirred for 2 days at room temperature. The reaction mixture was filtered to remove the precipitate and the filtrate was concentrated under reduced pressure. The residue was dissolved in 10 ml of water and washed twice with 10 ml of ethyl acetate. The aqueous layer was evaporated to dryness, dissolved in 5 ml of water, passed through a column (20 mm inner diameter) packed with 50 ml of CM-Sephadex ® C-25 (Na-type) and the column was eluted with 200 ml of 0.5M aqueous sodium chloride solution (10 ml fraction size). Fractions No. 17 to No. 30 were combined, evaporated to dryness and extracted 3 times with methanol. The methanol solution was passed through a column (20 mm inner diameter) packed with 150 ml of Sephadex ® LH-20 and developed with methanol (5 ml fraction size). Fractions No. 9 to No. 16 were combined and evaporated to dryness. The residue, weighing 950 mg, was crystallized from ethanol-acetone to obtain 790 mg (89.5% yield) of 7-guanidino-2-heptenamide hydrochloride having a melting point of 162°–168° C.

Proton NMR (measured in deuteromethanol), δ: 1.4–1.8 ($CH_2 \times 2$); 2.27 ($CH_2$); 3.20 ($CH_2$); 5.98 (CH); 6.80 (CH).

Infrared absorption spectrum (KBr tablet), $cm^{-1}$: 3370, 3150, 1660, 1625, 1610, 1590, 1415, 1395, 1370.

REFERENCE EXAMPLE 3

Synthesis of 7-guanidinoheptanamide hydrochloride

To a solution of 441 mg (2 mmoles) of 7-guanidino-2-heptenamide hydrochloride in 7 ml of methanol was added 47.5 mg (0.2 mmole) of nickel chloride. To the mixture, while being stirred at room temperature, was added 189 mg (5 mmoles) of sodium borohydride in small portions. After the addition, the mixture was further stirred for 1.5 hours, then filtered from a black precipitate, and the filtrate was evaporated to dryness. The residue was dissolved in 5 ml of 0.5M aqueous sodium chloride solution, passed through a column (30 mm inner diameter) packed with 100 ml of Diaion ® HP-20, and developed with 300 ml of 0.5M aqueous sodium chloride solution, then with 300 ml of water (15 ml fraction size. Fractions No. 25 to No. 33 were combined, evaporated to dryness and extracted 3 times with 5 ml of methanol. The methanol layer was passed through a column (20 mm inner diameter) packed with 150 ml of Sephadex ® LH-20, and developed with methanol (5 ml fraction size). The fractions No. 8 to No. 13 were combined, evaporated to dryness and crystallized from ethanol-acetone to yield 372 mg (83.5% yield) of colorless crystals of 7-guanidinoheptanamide hydrochloride having a melting point of 140°–141° C.

Proton NMR (measured in deuteromethanol), δ: 1.2–1.9 ($CH_2 \times 4$); 2.23 ($CH_2$); 3.20 ($CH_2$).

Infrared absorption spectrum (KBr tablet), $cm^{-1}$: 3350, 3150, 2920, 1655, 1630, 1590, 1455, 1430, 1400, 1220, 1165, 1130, 1065.

REFERENCE EXAMPLE 4

Synthesis of 8-guanidino-3-hydroxyoctanamide (a) Synthesis of 8-benzyloxycarbonylamino-3-ketooctanoic acid ethyl ester:

To a solution of 6.56 g (50 mmoles) of 6-aminohexanoic acid in 25 ml of 2N aqueous sodium hydroxide solution was added 5 ml of ethyl ether. To the mixture, while being cooled in ice and stirred, were added dropwise over a period of 30 minutes 10 ml of benzyloxycarbonyl chloride and 37.5 ml of 2N aqueous sodium hydroxide solution. After the addition, the temperature was brought back to room temperature and the stirring was continued for 2 hours. The reaction mixture was washed twice with 20 ml of ethyl ether. The aqueous layer was acidified with concentrated hydrochloric acid and extracted 3 times with 50 ml of ethyl acetate. The extract solutions were combined, washed with saturated saline, dried over anhydrous sodium sulfate and freed from the solvent by distillation to obtain 12.16 g (92% yield) of 6-benzyloxycarbonylaminohexanoic acid with a melting point of 127°–128° C.

A solution of 2.65 g (10 mmoles) of 6-benzyloxycarbonylaminohexanoic acid and 1.62 g (10 mmoles) of commercial 1,1'-carbonyldiimidazole in 25 ml of anhydrous tetrahydrofuran was stirred for 15 minutes at room temperature. To the reaction mixture was added a suspension of 6.18 g (40 mmoles) of a white powder of magnesium enolate of monoethyl malonate (prepared from 5.28 g of monoethyl malonate and 972 mg of magnesium) in 50 ml of anhydrous tetrahydrofuran. The mixture was stirred for 2 hours at room temperature. After addition of 50 ml of 1N hydrochloric acid and stirring for 10 minutes, the reaction mixture was extracted 3 times with 50 ml of chloroform. The chloroform layer was washed successively with 1N hydrochloric acid, saturated aqueous sodium hydrogen carbonate solution and saturated saline, then dried over anhydrous sodium sulfate and freed from the solvent by distillation. The residue was passed through a column of 100 g of "Silica Gel 60" (Merck & Co.) and eluted with chloroform (20 g fraction size). Fractions No. 43 to No. 105 were combined and evaporated to dryness to yield 2.35 g (70% yield) of ethyl 8-benzyloxycarbonylamino-3-ketooctanoate.

Proton NMR spectrum (in deuterochloroform), δ: 1.27 ($CH_3$); 1.1–1.9 ($CH_2 \times 3$); 2.52 ($CH_2$); 3.17 ($NCH_2$); 3.40 ($CH_2$); 4.18 ($CH_2$); 5.05 (NH); 5.09 ($CH_2$); 7.32 ($C_6H_5$).

Infrared absorption spectrum (KBr tablet), $cm^{-1}$: 3360, 2920, 1730, 1710, 1520, 1240.

(b) Synthesis of 8-guanidino-3-hydroxyoctanamide:

Into 20 ml of ethanol was dissolved 2.01 g (6 mmoles) of ethyl 8-benzyloxycarbonylamino-3-ketooctanoate obtained above in (a). To the solution was added portionwise with stirring at room temperature 227 mg (6 mmoles) of sodium borohydride. The mixture was stirred for 30 minutes, then admixed with several drops of acetic acid, poured into 100 ml of water and extracted three times with 50 ml of chloroform. The chloroform layers were combined, washed successively with 1N hydrochloric acid, saturated aqueous sodium hydrogen carbonate solution and saturated saline, then dried over anhydrous sodium sulfate and freed from the solvent by distillation to yield 2.00 g (99% yield) of ethyl 8-benzyloxycarbonylamino-3-hydroxyoctanoate with a melting point of 47°–50° C.

Into 40 ml of methanol saturated with gaseous ammonia was dissolved 1.69 g (5 mmoles) of ethyl 8-benzyloxycarbonylamino-3-hydroxyoctanoate. The solution was stirred for 3 days at room temperature, and the reaction mixture was evaporated to dryness. The residue was crystallized from ethanol to yield 1.18 g (72.5% yield) of 8-benzyloxycarbonylamino-3-hydroxyoctanamide having a melting point of 100°–101° C.

To a solution of 1.04 g (3.2 mmoles) of 8-benzyloxycarbonylamino-3-hydroxyoctanamide in 20 ml of methanol were added 3.2 ml of 1N hydrochloric acid and 200 mg of 10% palladium-carbon. The mixture was stirred under a hydrogen stream at room temperature for 3 hours. The catalyst was removed by filtration and the filtrate was evaporated to dryness to yield 670 mg of 8-amino-3-hydroxyoctanamide hydrochloride.

To a solution of 670 mg of 8-amino-3-hydroxyoctanamide hydrochloride in 8 ml of 1N aqueous sodium hydroxide solution, was added 668 mg (2.4 mmoles) of S-methylisothiourea hemisulfate. The mixture was stirred overnight at room temperature. The reaction mixture was adjusted to pH 6 with 1N hydrochloric acid, evaporated to dryness and dissolved in 5 ml of 1M saline. The solution was passed through a column of 160 ml of Diaion ® HP-20 (Mitsubishi Chemical Co.) and the column was eluted successively with 400 ml of 1M saline, 400 ml of 0.8M saline and 800 ml of 0.6M saline (15 g fraction size). Fractions No. 41 to No. 87 were combined, evaporated to dryness and extracted three times with 10 ml of methanol. The methanol layer was passed through a column of 300 ml of Sephadex ® LH-20 and eluted with methanol to effect desalting (7 ml fraction size). Fractions No. 25 to 35 were combined and evaporated to dryness to obtain 687 mg (85% yield) of 8-guanidino-3-hydroxyoctanamide hydrochloride.

Proton NMR spectrum (in deuteromethanol), δ: 1.4–1.8 ($CH_2 \times 4$); 2.36 ($CH_2$); 3.20 ($NCH_2$); 3.95 (CH).

Infrared absorption spectrum (KBr tablet), $cm^{-1}$: 3350, 3170, 2930, 1655, 1400, 1175.

REFERENCE EXAMPLE 5

Synthesis of 8-guanidino-2-octenamide

In a manner similar to that in the synthesis of 7-guanidino-2-heptenamide in Reference Example 2, 218 mg (86% yield) of 8-guanidino-2-octenamide hydrochloride having a melting point of 163°–165° C. was obtained from 270 mg of 8-guanidino-3-hydroxyoctanamide hydrochloride.

Proton NMR spectrum (in deuteromethanol), δ: 1.4–1.9 (CH$_2$×3); 2.25 (CH$_2$); 3.19 (NCH$_2$); 5.94 (CH); 6.79 (CH).

Infrared absorption spectrum (KBr tablet), cm$^{-1}$: 3400, 3120, 2920, 1660, 1630, 1400.

REFERENCE EXAMPLE 6

Synthesis of 9-guanidino-3-hydroxynonamide

In a manner similar to that in the synthesis of 8-guanidino-3-hydroxyoctanamide in Reference Example 4, 892 mg of 9-guanidino-3-hydroxynonamide hydrochloride was obtained from 2.56 g of 7-aminoheptanoic acid.

Proton NMR spectrum (in deuteromethanol), δ: 1.2–1.9 (CH$_2$×5); 2.35 (CH$_2$); 3.19 (NCH$_2$); 3.92 (CH).

Infrared absorption spectrum (KBr tablet), cm$^{-1}$: 3350, 3180, 2940, 1660, 1400, 1175.

REFERENCE EXAMPLE 7

Synthesis of 9-guanidino-2-nonenamide

In a manner similar to that in the synthesis of 7-guanidino-2-heptenamide in Reference Example 2, 253 mg (75% yield) of 9-guanidino-2-nonenamide hydrochloride was obtained from 361 mg of 9-guanidino-3-hydroxynonanamide hydrochloride; melting point, 132°–135° C.

Proton NMR spectrum (deuteromethanol), δ: 1.2–1.9 (CH$_2$×4); 2.23 (CH$_2$); 3.20 (NCH$_2$); 5.97 (CH); 6.80 (CH).

Infrared absorption spectrum (KBr tablet), cm$^{-1}$: 3350, 3175, 2940, 1660, 1620, 1420.

REFERENCE EXAMPLE 8

Synthesis of N-[4-(3-aminopropyl)aminobutyl]-2,2-dihydroxyethanamide

(a) Synthesis of mono-N-benzyloxycarbonyl-1,4-butanediamine

To a solution of 1.76 g (20 mmoles) of 1,4-butanediamine in 30 ml of 50% aqueous methanol was added 5.48 g (20 mmoles) of benzyl S-4,6-dimethylpyrimid-2-ylthiocarbonate (Kokusan-Kagaku Co.). The mixture was stirred for 3 hours. The reaction mixture was filtered to remove the precipitate [2.08 g (29%) of di-N-benzyloxycarbonyl compound was obtained from the precipitate]. The filtrate was evaporated to dryness, dissolved in 250 ml of chloroform and washed five times with 100 ml of water. The chloroform layer was dried over anhydrous sodium sulfate and evaporated to dryness to obtain 1.0 g (23% yield) of mono-N-benzyloxycarbonyl-1,4-butanediamine, a colorless syrup.

(b) Synthesis of O-tosyl-3-tert-butoxycarbonylamino-1-propanol

To a solution of 1.5 g (20 mmoles) of 3-amino-1-propanol in 30 ml of methanol was added 4.8 g (20 mmoles) of tert-butyl S-4,6-dimethylpyrimid-2-ylthiocarbonate. The mixture was stirred for 6 hours. The reaction mixture was evaporated to dryness, dissolved in 200 ml of chloroform and washed with 200 ml of water. The chloroform layer was concentrated and subjected to column chromatography using 300 g of silica gel (Wakogel ® C-200) and a toluene-ethyl acetate (1:1 by volume) mixture as developing solvent (15 ml fraction size). Fractions No. 82 to 151 were combined and evaporated to dryness to yield 2.95 g (84% yield) of 3-tert-butoxycarbonylamino-1-propanol, a colorless oily substance.

To a solution of 2.95 g (16.9 mmoles) of 3-tert-butoxycarbonylamino-1-propanol in 50 ml of pyridine, while being cooled in ice under an argon atmosphere, was added dropwise over a period of 40 minutes a pyridine solution containing 3.36 g (17.7 mmoles) of p-toluenesulfonyl chloride. The mixture was left standing overnight at 7° C., then admixed with a small volume of water and evaporated to dryness. The residue was dissolved in 200 ml of chloroform, washed successively with 5% aqueous potassium hydrogensulfate solution, saturated aqueous sodium hydrogencarbonate solution and water, then dried over anhydrous sodium sulfate and evaporated to dryness. The residue was subjected to column chromatography using 120 g of silica gel (Wakogel ® C-200) and a toluene-ethyl acetate (8:1 by volume) mixture as developing solvent (15 ml fraction size). Fractions No. 35 to No. 68 were combined and evaporated to dryness to yield 3.06 g (55% yield) of O-tosyl-3-tert-butoxycarbonylamino-1-propanol, a colorless oily substance.

(c) Synthesis of N-tert-butoxycarbonyl-N-(tert-butoxycarbonylaminopropyl)-1,4-butanediamine Into 15 ml of N,N-dimethylformamide was dissolved 800 mg (2.43 mmoles) of the O-tosyl-3-tert-butoxycarbonylamino-1-propanol obtained above in (b). After addition of 510 mg (4.8 mmoles) of lithium bromide (LiBr.H$_2$O), the mixture was stirred at room temperature for 24 hours. To the reaction mixture containing the bromine compound were added 540 mg (2.43 mmoles) of mono-N-benzyloxycarbonyl-1,4-butanediamine obtained above in (a) and 0.34 ml of triethylamine. The mixture was stirred at room temperature for 48 hours. To the reaction mixture was added 699 mg (2.9 mmoles) of tert-butyl S-4,6-dimethylpyrimid-2-ylthiocarbonate. The mixture was stirred for 13 hours at room temperature. The reaction mixture was evaporated to dryness, dissolved in 100 ml of chloroform, washed with 50 ml of water, dried over anhydrous sodium sulfate and evaporated to dryness. The residue was subjected to column chromatography using 200 g of silica gel (Wakogel ® C-200) and a toluene-ethyl acetate (4:1 by volume) mixture as developing solvent (12 ml fraction size). Fractions No. 134 to 165 were combined and evaporated to dryness to obtain 608 mg (52% yield) of N-benzyloxycarbonyl-N'-tert-butoxycarbonyl-N'-(tert-butoxycarbonylaminopropyl)-1,4-butanediamine, a colorless syrupy substance.

To a solution of 144 mg (0.3 mmoles) of the above syrupy substance in 5 ml of methanol was added 100 mg of 5% palladium-barium carbonate. The mixture was stirred under a hydrogen stream at room temperature for 5 hours. After removing the catalyst by filtration, the filtrate was evaporated to dryness to obtain 103 mg (100% yield) of N-tert-butoxycarbonyl-N'-(tert-butoxycarbonylaminopropyl)-1,4-butanediamine.

(d) Synthesis of N-[4-(3-aminopropyl)aminobutyl]-2,2-dihydroxyethanamide:

Into 2 ml of ethyl acetate were dissolved 100 mg (0.29 mmoles) of the N-tert-butoxycarbonyl-N-(tert-butoxycarbonylaminopropyl)-1,4-butanediamine obtained above in (c) and 148 mg (1 mmole) of 2,2-diethoxyacetic acid. To the resulting solution were added 135 mg (1 mmole) of 1-hydroxybenzotriazole and 206 mg (1 mmole) of dicyclohexylcarbodiimide. The mixture was stirred at room temperature for 15 hours. The precipitate was separated by filtration and washed with cold ethyl acetate. The filtrate and the washings were combined and washed with 1M aqueous ammonia, then with water. The ethyl acetate layer was dried over anhydrous sodium sulfate, evaporated to dryness and subjected to column chromatography using a column of 20 g of silica gel (Wakogel ® C-200) and a toluene-ethyl acetate (1:2 by volume) mixture as developing solvent (3 ml fraction size). The fractions No. 14 to No. 21 were combined and evaporated to dryness to yield 109 mg (79% yield) of N-[4-(3-tert-butoxycarbonylaminopropyl)-4-tert-butoxycarbonylaminobutyl]-2,2-diethoxyethanamide, a colorless syrupy substance.

To a solution of 44 mg (0.13 mmole) of the above syrupy substance in 1 ml of dioxane was added 2.5 ml of 0.1N hydrochloric acid. The mixture was stirred in an oil bath at 100° C. for 4 hours. The reaction mixture was neutralized with 0.2N aqueous sodium hydroxide solution to pH 6 and evaporated to dryness. The residue was extracted with 1.5 ml of methanol and the methanol layer was passed through a column (16.5 mm inner diameter) packed with 100 ml of Sephadex ® LH-20 and developed with methanol (2 ml fraction size). Fractions No. 22 to No. 25, positive to ninhydrin reaction, were combined and evaporated to dryness, yielding 13 mg (46% yield) of N-[4-(3-aminopropyl)aminobutyl]-2,2-dihydroxyethanamide dihydrochloride, a colorless syrupy substance.

EXAMPLE 1

Synthesis of N-[4-(3-aminopropyl)aminobutyl]-2-(4-guanidinobutanamido)-2-hydroxyethanamide A mixture of 360 mg (2 mmoles) of 4-guanidinobutanamide hydrochloride, 701 mg (2.4 mmole) of N-[4-(3-aminopropyl)aminobutyl]-2,2-dihydroxyethanamide dihydrochloride, 264 mg (2 mmoles) of glutaric acid and 0.36 ml of water was heated at 60° C. for 24 hours. After completion of the reaction, 5 ml of water was added to the reaction mixture, then passed through a column (20 mm inner diameter) packed with 150 ml of CM-Sephadex ® C-25 (Na-type), and fractionated by the gradient elution method with 1.5 liters of water and 1.5 liters of 0.8M aqueous sodium chloride solution (15 ml fraction size). The fractions No. 125 to No. 137 corresponding to the sodium chloride concentrations of 0.48–0.56M were combined, then concentrated, and extracted three times with 10 ml of methanol. The methanol layer was passed through a column (20 mm inner diameter) packed with 150 ml of Sephadex ® LH-20, and developed with methanol (7 ml fraction size). The fractions No. 9 to No. 15 were combined and evaporated to dryness, yielding 318 mg (35% yield) of a white powder of N-[4-(3-aminopropyl)aminobutyl]-2-(4-guanidinobutanamido)-2-hydroxyethanamide hydrochloride.

EXAMPLE 2

Synthesis of N-[4-(3-aminopropyl)aminobutyl]-2-(5-guanidinopentanamido)-2-hydroxyethanamide A mixture of 92.4 mg (0.48 mmole) of 5-guanidinopentanamide hydrochloride, 166.5 mg (0.57 mmole) of N-[4-(3-aminopropyl)aminobutyl]-2,2-dihydroxyethanamide dihydrochloride, 62.8 mg (0.48 mmole) of glutaric acid and 0.1 ml of water was heated at 60° C. for 24 hours. After completion of the reaction, 5 ml of water was added to the reaction mixture which was then purified in a manner similar to that in Example 1 using CM-Sephadex ® C-25 (Na-type) and Sephadex ® LH-20 to obtain 82.5 mg (37.1% yield) of a white powder of N-[4-(3-aminopropyl)aminobutyl]-2-(5-guanidinopentanamido)-2-hydroxyethanamide trihydrochloride.

EXAMPLE 3

Synthesis of N-[4-(3-aminopropyl)aminobutyl]-2-(6-guanidinohexanamido)-2-hydroxyethanamide A mixture of 446 mg (2.14 mmoles) of 6-guanidinohexanamide hydrochloride, 750 mg (2.57 mmoles) of N-[4-(3-aminopropyl)aminobutyl]-2,2-dihydroxyethanamide dihydrochloride, 283 mg (2.14 mmoles) of glutaric acid and 0.45 ml of water was heated at 60° C. for 24 hours. After completion of the reaction, 5 ml of water was added to the reaction mixture and the resulting mixture was purified in a manner similar to that in Example 1, using CM-Sephadex ® C-25 (Na-type) and Sephadex ® LH-20 to obtain 459 mg (44% yield) of a white powder of N-[4-(3-aminopropyl)aminobutyl]-2-(6-guanidinohexanamido)-2-hydroxyethanamide trihydrochloride.

EXAMPLE 4

Synthesis of N-[4-(3-aminopropyl)aminobutyl]-2-(7-guanidinoheptanamido)-2-hydroxyethanamide A mixture of 360 mg (1.62 mmoles) of 7-guanidinoheptanamide hydrochloride, 568 mg (1.94 mmoles) of N-[4-(3-aminopropyl)aminobutyl]-2,2-dihydroxyethanamide dihydrochloride, 214 mg (1.62 mmoles) of glutaric acid and 0.36 ml of water was heated at 60° C. for 24 hours. After completion of the reaction, 5 ml of water was added to the reaction mixture and the resulting mixture was purified in a manner similar to that in Example 1, using CM-Sephadex ® C-25 (Na-type) and Sephadex ® LH-20 to obtain 317 mg (39% yield) of a white powder of N-[4-(3-aminopropyl)aminobutyl]-2-(7-guanidinoheptanamido)-2-hydroxyethanamide trihydrochloride.

EXAMPLE 5

Synthesis of N-[4-(3-aminopropyl)aminobutyl]-2-(8-guanidinooctanamido)-2-hydroxyethanamide A mixture of 500 mg (2.11 mmoles) of 8-guanidinooctanamide hydrochloride, 740 mg (2.53 mmoles) of N-[4-(3-aminopropyl)aminobutyl]-2,2-dihydroxyethanamide dihydrochloride, 335 mg (2.53 mmoles) of glutaric acid and 0.34 ml of water was heated at 60° C. for 24 hours.

After completion of the reaction, 5 ml of water was added to the reaction mixture and the resulting mixture was purified in a manner similar to Example 1, using CM-Sephadex ® C-25 (Na-type) and Sephadex ® LH-20, to yield 526 mg (49% yield) of a white powder of N-[4-(3-aminopropyl)aminobutyl]-2-(8-guanidinooctanamido)-2-hydroxyethanamide trihydrochloride.

EXAMPLE 6

Synthesis of N-[4-(3-aminopropyl)aminobutyl]-2-(9-guanidinononanamido)-2-hydroxyethanamide A mixture of 316 mg (1.26 mmoles) of 9-guanidinononanamide hydrochloride, 442 mg (1.51 mmoles) of N-[4-(3-aminopropyl)aminobutyl]-2,2-dihydroxyethanamide dihydrochloride, 166 mg (1.26 mmoles) of glutaric acid and 0.01 ml of water was heated at 60° C. for 24 hours. After completion of the reaction, 5 ml of water was added to the reaction mixture and the mixture was purified in a manner similar to that in Example 1, using CM-Sephadex ® C-25 (Na-type) and Sephadex ® LH-20 to yield 324 mg (49% yield) of a white powder of N-[4-(3-aminopropyl)aminobutyl]-2-(9-guanidinononanamido)-2-hydroxyethanamide trihydrochloride.

EXAMPLE 7

Synthesis of N-[4-(3-aminopropyl)aminobutyl]-2-(4-guanidinobutanamido)-2-methoxyethanamide To a solution of 45.5 mg (0.10 mmole) of N-[4-(3-aminopropyl)aminobutyl]-2-(4-guanidinobutanamido)-2-hydroxyethanamide trihydrochloride in 1 ml of anhydrous methanol was added 0.1 ml of 2N hydrogen chloride-methanol. The mixture was stirred at room temperature for 17 hours. The reaction mixture was concentrated under reduced pressure and dissolved in 3 ml of water. The resulting solution was passed through a column (20 mm inner diameter) packed with 150 ml of CM-Sephadex ® C-25 and fractionated by the gradient method with each one liter of water and 1M aqueous sodium chloride solution (17 ml fraction size). The fractions No. 67 to No. 71 corresponding to the salt concentrations of 0.63–0.67M were combined, evaporated to dryness and extracted three times with 5 ml of methanol. The methanol layer was passed through a column (20 mm inner diameter) packed with 150 ml of Sephadex ® LH-20 and developed with methanol (7 ml fraction size). Fractions No. 10 to No. 14 were combined and evaporated to dryness, yielding 31.4 mg (67% yield) of a white powder of N-[4-(3-aminopropyl)aminobutyl]-2-(4-guanidinobutanamido)-2-methoxyethanamide trihydrochloride.

EXAMPLE 8

Synthesis of N-[4-(3-aminopropyl)aminobutyl]-2-(6-guanidinohexanamido)-2-methoxyethanamide To a solution of 177 mg (0.37 mmole) of N-[4-(3-aminopropyl)aminobutyl]-2-(6-guanidinohexanamido)-2-hydroxyethanamide trihydrochloride in 3.6 ml of anhydrous methanol was added 0.36 ml of 2N hydrogen chloride-methanol. The mixture was stirred at room temperature for 17 hours. The reaction mixture was concentrated under reduced pressure and the resulting white powder was purified in a manner similar to that in Example 7, using CM-Sephadex ® C-25 (Na-type) and Sephadex ® LH-20 to yield 110 mg (60% yield) of a white powder of N-[4-(3-aminopropyl)aminobutyl]-2-(6-guanidinohexanamido)-2-methoxyethanamide trihydrochloride.

EXAMPLE 9

Synthesis of N-[4-(3-aminopropyl)aminobutyl]-2-(7-guanidinoheptanamido)-2-methoxyethanamide To a solution of 920 mg (1.85 mmoles) of N-[4-(3-aminopropyl)aminobutyl]-2-(7-guanidinoheptanamido)-2-hydroxyethanamide trihydrochloride in 20 ml of anhydrous methanol was added 2 ml of 2N hydrogen chloride-methanol. The mixture was stirred at room temperature for 15 hours. The reaction mixture was concentrated under reduced pressure and the resulting white powder was dissolved in 15 ml of water. The aqueous solution was adjusted to pH 6 with 1N aqueous sodium hydroxide solution, then passed through a column (25 mm inner diameter) packed with 300 ml of CM-Sephadex ® C-25 (Na-type) and fractionated by the gradient elution method with each 2 liters of water and 1M aqueous sodium chloride solution (fraction size, 17 ml). The fractions No. 138 to No. 152 corresponding to the sodium chloride concentrations of 0.59–0.65M were combined, evaporated to dryness and extracted twice with 10 ml of methanol. The methanol layer was passed through a column (25 mm inner diameter) packed with 300 ml of Sephadex ® LH-20 and developed with methanol (fraction size, 7 ml). Fractions No. 18 to No. 32 were combined and evaporated to dryness, yielding 607 mg (64% yield) of a white powder of N-[4-(3-aminopropyl)aminobutyl]-2-(7-guanidinoheptanamido)-2-methoxyethanamide trihydrochloride.

EXAMPLE 10

Synthesis of N-[4-(3-aminopropyl)aminobutyl]-2-(8-guanidinooctanamido)-2-methoxyethanamide To a solution of 220 mg (0.43 mmole) of N-[4-(3-aminopropyl)aminobutyl]-2-(8-guanidinooctanamido)-2-hydroxyethanamide trihydrochloride in 4.4 ml of anhydrous methanol was added 0.44 ml of 2N hydrogen chloride-methanol. The mixture was stirred overnight at room temperature. The reaction mixture was concentrated under reduced pressure and the resulting white powder was purified in a manner similar to that in Example 7, using CM-Sephadex ® C-25 (Na-type) and Sephadex ® LH-20 to yield 195 mg (86% yield) of a white powder of N-[4-(3-aminopropyl)aminobutyl]-2-(8-guanidinooctanamido)-2-methoxyethanamide trihydrochloride.

EXAMPLE 11

Synthesis of N-[4-(3-aminopropyl)aminobutyl]-2-(9-guanidinononanamido)-2-methoxyethanamide To a solution of 160 mg (0.31 mmole) of N-[4-(3-aminopropyl)aminobutyl]-2-(9-guanidinononanamido)-2-hydroxyethanamide trihydrochloride in 3.2 ml of anhydrous methanol was added 0.32 ml of 2N hydrogen chloride-methanol. The mixture was stirred overnight at room temperature. The reaction mixture was concentrated under reduced pressure and the resulting white powder was purified in a manner as that in Example 7, using CM-Sephadex ® C-25 (Na-type) and Sephadex ® LH-20 to yield 107 mg (65% yield) of a white powder of N-[4-(3-aminopropyl)aminobutyl]-2-(9-guanidinononanamido)-2-methoxyethanamide trihydrochloride.

EXAMPLE 12

Synthesis of N-[4-(3-aminopropyl)aminobutyl]-2-(7-guanidinoheptanamido)-2-ethoxyethanamide To 100 mg (0.20 mmole) of N-[4-(3-aminopropyl)aminobutyl]-2-(7-guanidinoheptanamido)-2-hydroxyethanamide trihydrochloride were added 10 ml of anhydrous ethanol and 1 ml of anhydrous ethanol saturated with gaseous hydrogen chloride. The mixture was stirred at room temperature for 24 hours. The reaction mixture was filtered to remove the insolubles and the filtrate was concentrated under reduced pressure. The resulting white powder was purified in a manner similar to that in Example 7, using CM-Sephadex ® C-25 (Na-type) and Sephadex ® LH-20, to yield 71 mg (68% yield) of a white powder of N-[4-(3-aminopropyl)aminobutyl]-2-(7-guanidinoheptanamido)-2-ethoxyethanamide trihydrochloride.

EXAMPLE 13

Synthesis of N-[4-(3-aminopropyl)aminobutyl]-2-(7-guanidinoheptanamido)-2-butoxyethanamide To 100 mg (0.20 mmole) of N-[4-(3-aminopropyl)aminobutyl]-2-(7-guanidinoheptanamido)-2-hydroxyethanamide trihydrochloride were added 10 ml of n-butanol and 1 ml of n-butanol saturated with gaseous hydrogen chloride. The mixture was stirred at room temperature for 2 days. The reaction mixture was filtered to remove the insolubles and the filtrate (n-butanol solution) was extracted three times with 5 ml of water. The aqueous layer was neutralized with Amberlite ® IR-410 and concentrated under reduced pressure. The residue was purified in a manner similar to that in Example 7, using CM-Sephadex ® C-25 (Na-type) and Sephadex ® LH-20, to yield 15 mg (13.5% yield) of a white powder of N-[4-(3-aminopropyl)aminobutyl]-2-(7-guanidinoheptanamido)-2-butoxyethanamide trihydrochloride.

EXAMPLE 14

Synthesis of N-[4-(3-aminopropyl)aminobutyl]-2-(7-guanidinoheptanamido)-2-(2-hydroxy)ethoxyethanamide To a solution of 100 mg (0.20 mmole) of N-[4-(3-aminopropyl)aminobutyl]-2-(7-guanidinoheptanamido)-2-hydroxyethanamide trihydrochloride in 5 ml of ethylene glycol was added 0.5 ml of ethylene glycol saturated with gaseous hydrogen chloride. The mixture was stirred overnight at room temperature. After addition of 25 ml of water, the reaction mixture was adjusted to pH 6 with 1N aqueous sodium hydroxide solution and purified in a manner similar to that in Example 7, using CM-Sephadex ® C-25 (Na-type) and Sephadex ® LH-20, to yield 63 mg (58% yield) of a white powder of N-(4-(3-aminopropyl)aminobutyl]-2-(7-guanidinoheptanamido)-2-(2-hydroxy)ethoxyethanamide trihydrochloride.

EXAMPLE 15

Synthesis of N-[4-(3-aminopropyl)aminobutyl]-2-(7-guanidinoheptanamido)-2-benzyloxyethanamide To 100 mg (0.20 mmole) of N-[4-(3-aminopropyl)aminobutyl]-2-(7-guanidinoheptanamido)-2-hydroxyethanamide trihydrochloride were added 10 ml of benzyl alcohol and 1 ml of benzyl alcohol saturated with gaseous hydrogen chloride. The mixture was stirred at room temperature for 18 hours. The reaction mixture was filtered to remove insolubles and the benzyl alcohol layer was extracted three times with 5 ml of water. The aqueous layer was neutralized with Amberlite ® IR-410, evaporated to dryness and purified in a manner similar to that in Example 7 using CM-Sephadex ® C-25 (Na-type) and Sephadex ® LH-20 to yield 61 mg (52% yield) of a white powder of N-[4-(3-aminopropyl)aminobutyl]-2-(7-guanidinoheptanamido)-2-benzyloxyethanamide trihydrochloride.

EXAMPLE 16

Synthesis of N-[4-(3-aminopropyl)aminobutyl]-2-(7-guanidino-2-heptenamido)-2-hydroxyethanamide A mixture of 234.5 mg (1.06 mmoles) of 7-guanidino-2-heptenamide hydrochloride, 372.3 mg (1.27 mmoles) of N-[4-(3-aminopropyl)aminobutyl]-2,2-dihydroxyethanamide dihydrochloride, 140.4 mg (1.06 mmoles) of glutaric acid and 0.2 ml of water was heated at 60° C. for 24 hours. After completion of the reaction, the reaction mixture was purified in a manner similar to that in Example 1 using CM-Sephadex ® C-25 (Na-type) and Sephadex ® LH-20 to obtain 244.6 mg (46.5% yield) of a white powder of N-[4-(3-aminopropyl)aminobutyl]-2-(7-guanidino-2-heptenamido)-2-hydroxyethanamide trihydrochloride.

EXAMPLE 17

Synthesis of N-[4-(3-aminopropyl)aminobutyl]-2-(8-guanidino-2-octenamido)-2-hydroxyethanamide A mixture of 202.4 mg (0.86 mmole) of 8-guanidino-2-octenamide hydrochloride, 302.4 mg (1.04 mmoles) of N-[4-(3-aminopropyl)aminobutyl]-2,2-dihydroxyethanamide dihydrochloride, 113.9 mg (0.86 mmole) of glutaric acid and 0.2 ml of water was heated at 60° C. for 24 hours. After completion of the reaction, the reaction mixture was purified in a manner similar to that in Example 1 using CM-Sephadex ® C-25 (Na-type) and Sephadex ® LH-20 to obtain 128.3 mg (29.2% yield) of N-[4-(3-aminopropyl)aminobutyl]-2-(8-guanidino-2-octenamido)-2-hydroxyethanamide trihydrochloride.

EXAMPLE 18

Synthesis of N-[4-(3-aminopropyl)aminobutyl]-2-(9-guanidino-2-nonenamido)-2-hydroxyethanamide A mixture of 206.2 mg (0.84 mmole) of 9-guanidino-2-nonenamide hydrochloride, 291.0 mg (1.00 mmole) of N-[4-(3-aminopropyl)aminobutyl]-2,2-dihydroxyethanamide dihydrochloride, 109.6 mg (0.84 mmole) of glutaric acid and 0.2 ml of water was heated at 60° C. for 24 hours. After completion of the reaction, the reaction mixture was purified in a manner similar to that in Example 1 using CM-Sephadex ® C-25 (Na-type) and Sephadex ® LH-20 to obtain 135.0 mg (31.1% yield) of a white powder of N-[4-(3-aminopropyl)aminobutyl]-2-(9-guanidino-2-nonenamido-2-hydroxyethanamide trihydrochloride.

EXAMPLE 19

Synthesis of N-[4-(3-aminopropyl)aminobutyl]-2-(7-guanidino-2-heptenamido)-2-methoxyethanamide To a solution of 50.3 mg (0.10 mmole) of N-[4-(3-aminopropyl)aminobutyl]-2-(7-guanidino-2-heptenamido)-2-hydroxyethanamide trihydrochloride in 1 ml of anhydrous methanol was added 0.1 ml of 2N hydrogen chloride-methanol. The mixture was stirred overnight at room temperature and the reaction mixture was concentrated under reduced pressure. The residue was purified in a manner similar to that in Example 7 using CM-Sephadex ® C-25 (Na-type) and Sephadex ® LH-20 to obtain 37.2 mg (72.4% yield) of N-[4-(3-aminopropyl)aminobutyl]-2-(7-guanidino-2-heptenamido)-2-methoxyethanamide trihydrochloride.

EXAMPLE 20

Synthesis of N-[4-(3-aminopropyl)aminobutyl]-2-(8-guanidino-3-hydroxyoctanamido)-2-hydroxyethanamide A mixture of 150 mg (0.59 mmole) of 8-guanidino-3-hydroxyoctanamide hydrochloride, 208 mg (0.71 mmole) of N-[4-(3-aminopropyl)aminobutyl]-2,2-dihydroxyethanamide dihydrochloride, 78 mg (0.59 mmole) of glutaric acid and 0.1 ml of water was heated at 60° C. for 24 hours. After completion of the reaction, the reaction mixture was purified in a manner similar to that in Example 1 using CM-Sephadex ® C-25 (Na-type) and Sephadex ® LH-20 to yield 120.7 mg (38.6% yield) of a white powder of N-[4-(3-aminopropyl)aminobutyl]-2-(8-guanidino-3-hydroxyoctanamido)-2-hydroxyethanamide trihydrochloride.

EXAMPLE 21

Synthesis of N-[4-(3-aminopropyl)aminobutyl]-2-(9-guanidino-3-hydroxynonanamido)-2-hydroxyethanamide A mixture of 325.8 mg (1.23 mmoles) of 9-guanidino-3-hydroxynonanamide hydrochloride, 428.1 mg (1.47 mmoles) of N-[4-(3-aminopropyl)aminobutyl]-2,2-dihydroxyethanamide dihydrochloride, 161.4 mg (1.23 mmoles) of glutaric acid and 0.3 ml of water was heated at 60° C. for 24 hours. After completion of the reaction, the reaction mixture was purified in a manner similar to that in Example 1 using CM-Sephadex ® C-25 (Na-type) and and Sephadex ® LH-20 to yield 220.8 mg (33.4% yield) of a white powder of N-[4-(3-aminopropyl)aminobutyl]-2-(9-guanidino-3-hydroxynonanamido)-2-hydroxyethanamide trihydrochloride.

EXAMPLE 22

Synthesis of 11-O-methylspergualin

To a solution of 1.8 g (3.51 mmoles) of (−)-spergualin trihydrochloride in 35 ml of anhydrous methanol was added 3.5 ml of 2N hydrogen chloride-methanol. The mixture was stirred at room temperature for 15 hours. The reaction mixture was evaporated to dryness, then dissolved in 30 ml of water, passed through a column of CM-Sephadex ® C-25 (Na-type; 600 ml) and fractionated by the gradient elution method with each 3 liters of water and 1M aqueous sodium chloride solution (fraction size, 17 g). Fractions No. 208 to No. 230 were combined, evaporated to dryness and extracted three times with 10 ml of methanol. The methanol layer was passed through a column of Sephadex ® LH-20 (300 ml) and eluted with methanol to effect desalting (fraction size, 7 g). Fractions No. 19 to No. 33 were combined and evaporated to dryness to yield 1.528 g (82% yield) of a white powder of 11-O-methylspergualin trihydrochloride.

For the separation of 11-O-methylspergualin trihydrochloride into its epimeric components, use was made of HPLC on a column, 2 cm×25 cm, packed with Nucleosil ® 30C$_{18}$, a reversed phase packing material of M. Nagel Co., under the following conditions:

Flow rate: 10 ml/minute
Pressure: 30 kg/cm$^2$
Solvent: acetonitrile—[0.01M sodium pentanesulfonate+0.01M Na$_2$HPO$_4$ (pH 3)]=9:91
Charge: 6 mg
Detection: uv 205 nm In HPLC, the uv absorption peak for (−)-11-O-methylspergualin (retention time, 48.3 minutes) appeared first and that for (+)-11-O-methylspergualin (retention time, 56.5 minutes) followed. The fractionation was repeated 12 times. The fractions corresponding to each peak were collected and purified in a manner similar to that in Example 1 using CM-Sephadex ® C-25 (Na-type) and Sephadex ® LH-20 to obtain 32.9 mg of a white powder of (−)-11-O-methylspergualin trihydrochloride and 24.5 mg of a white powder of (+)-11-O-methylspergualin trihydrochloride.

EXAMPLE 23

Synthesis of 11-O-ethylspergualin

To 484 mg (0.94 mmole) of spergualin dihydrochloride [(−)-spergualin:(+)-spergualin=1:1] were added 20 ml of anhydrous ethanol and 2 ml of 2N hydrogen chloride-ethanol. The mixture was stirred at room temperature for 2 days. The reaction mixture was evaporated to dryness, then dissolved in 10 ml of water, adjusted to pH 4 with 1N aqueous sodium hydroxide solution and purified in essentially the same manner as in Example 22 using CM-Sephadex ® C-25 (Na-type) and Sephadex ® H-20, yielding 355.6 mg (70% yield) of a white powder of 11-O-ethylspergualin trihydrochloride.

For the separation of the 11-O-ethylspergualin trihydrochloride into its epimeric components, use was made of HPLC in essentially the same manner as in Example 22, except that the solvent used was a mixture of acetonitrile—[0.01M sodium pentanesulfonate+0.01M Na$_2$HPO$_4$ (pH 3)] (10.5:89.5). On repeated fractionation, 6 times in total, there were obtained 11 mg of a white powder of (−)-11-O-ethylspergualin trihydrochloride and 14.5 mg of a white powder of (+)-11-O-ethylspergualin trihydrochloride.

EXAMPLE 24

Synthesis of 11-O-n-butylspergualin

To 493 mg (0.96 mmole) of (−)-spergualin trihydrochloride were added 30 ml of n-butanol and 3 ml of n-butanol saturated with hydrogen chloride. The mixture was stirred at room temperature for 2 days. The n-butanol soluble portion of the reaction mixture was evaporated to dryness, then dissolved in 10 ml of water, adjusted to pH 4 with 1N aqueous sodium hydroxide solution and purified with CM-Sephadex ® C-25 (Na-type) and Sephadex ® LH-20 in essentially the same manner as in Example 22 to obtain 114.7 mg (21% yield) of a white powder of 11-O-n-butylspergualin trihydrochloride.

For the separation of the 11-O-n-butylspergualin trihydrochloride into its epimeric components, use was made of HPLC in essentially the same manner as in Example 22, except that the solvent used was a mixture of acetonitrile—[0.01M sodium pentanesulfonate+0.01M Na$_2$HPO$_4$ (pH 3)] (14.5:85.5). On repeated fractionation, 6 times in total, there were obtained 15 mg of a white powder of (−)-11-O-n-butylspergualin trihydrochloride and 16 mg of a white powder of (+)-11-O-n-butylspergualin trihydrochloride.

EXAMPLE 25

Synthesis of 11-O-(2-hydroxy)ethylspergualin

To a solution of 2.88 g (5.61 mmoles) of (−)-spergualin trihydrochloride in 100 ml of ethylene glycol was added 10 ml of ethylene glycol saturated with hydrogen chlorine. The mixture was stirred at room temperature for 24 hours. After addition of 200 ml of water, the reaction mixture was adjusted to pH 4 with 1N aqueous sodium hydroxide solution and purified with CM-Sephadex ® C-25 (Na-type) and Sephadex ® LH-20 in essentially the same manner as in Example 22 to yield 2.7 g (73% yield) of a white powder of 11-O-(2-hydroxy)ethylspergualin trihydrochloride.

For the separation of the 11-O-(2-hydroxy)ethylspergualin trihydrochloride into its epimeric components, use was made of HPLC as in Example 22, except that the solvent and charge were as follows:

Solvent: acetonitrile—[0.01M sodium pentanesulfonate+0.01M Na$_2$HPO$_4$ (pH 3)] (7:93)
Charge: 20 mg On repeated fractionation, 6 times in total, there were obtained 2.3 mg of a white powder of (−)-11-O-(2-hydroxy)ethylspergualin trihydrochloride and 2.5 mg of a white powder of (+)-11-O-(2-hydroxy)ethylspergualin trihydrochloride.

EXAMPLE 26

Synthesis of 11-O-benzylspergualin

To 2.36 g (4.60 mmoles) of (−)-spergualin trihydrochloride were added 90 ml of benzyl alcohol and 9 ml of benzyl alcohol saturated with hydrogen chloride. The mixture was stirred at room temperature overnight. The reaction mixture was extracted with 350 ml of water and the aqueous layer was adjusted to pH 6.0 with 1N aqueous sodium hydroxide solution and concentrated to dryness. The residue was dissolved in 20 ml of 1M aqueous sodium chloride solution, passed through a column of 500 ml of Diaion ® HP-20 (Mitsubishi Chemical Co.) and eluted successively with each 1.5 liters of 0.6M saline, 0.4M saline and water. The portion eluted with water was evaporated to dryness and desalted with Sephadex ® LH-20 as in Example 1 to yield 1.92 g (69% yield) of a white powder of 11-O-benzylspergualin trihydrochloride.

For the separation of the 11-O-benzylspergualin trihydrochloride into its epimeric components, use was made of HPLC which was carried out in the same manner as in Example 22, except that the solvent used was a mixture of acetonitrile—[0.01M sodium pentanesulfonate +0.01M NaHD 2HPO$_4$ (pH 3)] (16:84). On repeated fractionation, 9 times in total, there were obtained 21.2 mg of a white powder (−)-11-O-benzylspergualin trihydrochloride and 18.8 mg of a white powder of (+)-11-O-benzylspergualin trihydrochloride.

EXAMPLE 27

Synthesis of (−)-11-O-methylspergualin (a) (−)-1-N,4-bis(benzyloxycarbonyl)spergualin To a solution of 2.3 g (4.48 mmoles) of (−)-spergualin trihydrochloride in a mixture of 11 ml of N,N-dimethylformamide and 11 ml of water, while being cooled in ice, was added 1.25 ml (8.96 mmoles) of triethylamine followed by a solution of 2.24 g (8.97 mmoles) of N-benzyloxycarbonyloxysuccinimide in 11 ml of N,N-dimethylformamide. The mixture was stirred for 15 hours at 5° C. The reaction mixture was concentrated under reduced pressure, dissolved in 10 ml of 0.5M aqueous sodium chloride solution, then passed through a column of Diaion ®HP-20 (400 ml) equilibrated with 0.5M aqueous sodium chloride solution, washed with 1 liter of 0.5M saline, then with 1 liter of water and eluted with methanol (fraction size, 15 g). Fractions No. 21 to No. 30 were combined and evaporated to dryness to yield 287 mg (82% yield) of a white powder of (−)-1-N,4-bis(benzyloxycarbonyl)spergualin hydrochloride; $[\alpha]_D^{21} -11°$ (c 1, water).

Proton NMR (in deuteromethanol), δ: 1.3–2.0 (CH$_2$×6), 2.38 (CH$_2$), 2.9–3.4 (NCH$_2$×5), 4.0 (CH), 5.04 (CH$_2$), 5.07 (CH$_2$), 5.56 (CH), 7.30 (C$_6$H$_5$×2).

(b) (−)-1-N,4-bis(benzyloxycarbonyl)-11-O-methylspergualin

To a solution of 78 mg (0.484 mmole) of the above (−)-1-N,4-bis(benzyloxycarbonyl)spergualin hydrochloride in 12 ml of methylene chloride, while being cooled in ice, was added 2.44 ml (0.484 mmole) of a solution of 0.1 ml of boron trifluoride-ether complex in 4 ml of methylene chloride. To the mixture was added portionwise 9 ml (1 ml at a time interval of 30 minutes to one hour) of a solution of diazomethane in methylene chloride. [The diazomethane solution was prepared by gradually adding 10 g of N-nitrosomethylurea to a mixture of 30 ml of a 40% potassium hydroxide solution and 100 ml of methylene chloride while cooling at 40° C. in water; separating the organic layer and extracting the aqueous layer with 10 ml of methylene chloride; combining the organic layers and drying over granular potassium hydroxide at 5° C. for 3 hours.] After 3.5 hours from the start of reaction, stirring was discontinued. After addition of several drops of dilute acetic acid, the reaction mixture was concentrated under reduced pressure, then dissolved in 3 ml of 50% aqueous methanol, passed through a column of Diaion ®HP-20 (100 ml), washed with 300 ml of 10% aqueous methanol and eluted with methanol (fraction size, 15 ml). Fractions No. 25 to No. 28 were combined and evaporated to dryness, yielding 262.4 mg of a white powder of a mixture of (−)-1-N,4-bis(benzyloxycarbonyl)-11-O-methylspergualin hydrochloride and unreacted (−)-1-N,4-bis(benzyloxycarbonyl)-spergualin hydrochloride (recovery, 69.2% by weight). The composition of this mixture was determined by HPLC on a column of Nucleosil ®5C$_{18}$ (4.0×150 mm), eluted with a mixture (1:1) of acetonitrile and 0.01M (NH$_4$)$_2$HPO$_4$ at a flow rate of 0.8 ml/min. It was found that the ratio between (−)-1-N,4-bis(benzyloxycarbonyl)-11-O-methylspergualin hydrochloride (retention time, 10.47 minutes), and (—)-1-N,4-bis(benzyloxycarbonyl)spergualin hydrochloride (retention time, 7.74 minutes) was 47:50.

The above mixture (78.5 mg) was passed through a column of 30 ml of Silicagel ®60 (Merck Co.) and eluted with a 10% methanol-chloroform mixture. The eluate was analyzed by HPLC carried out under the same conditions as described above. Fractions showing uv absorption at 200 nm at a retention time of 10.47 minutes were collected and evaporated to dryness, yielding 28.6 mg of a white powder of (—)-1-N,4-bis(-benzyloxycarbonyl)-11-O-methylspergualin hydrochloride; $[\alpha]_D^{25}-14.4°$ (c 1, methanol). Proton NMR (in deuteromethanol), δ: 1,3–2.0 (CH$_2$×6), 2.42 (CH$_2$), 2.9–3.4 (NCH$_2$×5), 3.37 (OCH$_3$), 4.0 (CH), 5.03 (CH$_2$), 5.08 (CH$_2$), 5.34 (CH), 7.29 (C$_6$H$_5$×2).

(c) (—)-11-O-methylspergualin

Into a mixture of 5 ml of ethanol, 5 ml of water and 0.36 ml of 1N-hydrochloric acid was dissolved 130 mg of the above mixture (47:50) of (—)-1-N,4-bis(benzyloxycarbonyl)-11-O-methylspergualin hydrochloride and (—)-1-N,4-bis(benzyloxycarbonyl)spergualin hydrochloride. After addition of 50 mg of 10% palladium-carbon to the solution, the mixture was stirred under a hydrogen stream for 4 hours at room temperature. The catalyst was removed by filtration and the filtrate was evaporated to dryness. The residue was dissolved in 3 ml of water, passed through a column of 150 ml of CM-Sephadex ®C-25 (Na-type) and fractionated by the gradient elution method with each 900 ml of water and 1M aqueous sodium chloride solution (fraction size, 17 g). Fractions No. 76 to No. 81 were combined and desalted as in Example 22, using Sephadex ®LH-20 to obtain 25.4 mg (51% yield) of a white powder of (—)-11-O-methylspergualin trihydrochloride; $[\alpha]_D^{25}-27.1°$ (c 1, water).

Fractions No. 83 to No. 86 of the eluate from the CM-Sephadex ®column were similarly desalted to recover 24.5 mg (52% recovery) of a white powder of (—)-spergualin trihydrochloride.

EXAMPLE 28

Synthesis of (—)-11-O-ethylspergualin

In a manner similar to that in Example 27(b), a methylene chloride solution of diazoethane was allowed to react with 352 mg (0.451 mmole) of the (—)-1-N,4-bis(-benzyloxycarbonyl)spergualin hydrochloride obtained in Example 27(a) to yield 217.0 mg of a mixture of (—)-1-N,4-bis(benzyloxycarbonyl)-11-O-ethylspergualin hydrochloride and unreacted (—)-1-N,4-bis(benzyloxycarbonyl)spergualin hydrochloride. The mixture was treated in essentially the same manner as in Example 27(c) to obtain 41.7 mg of a white powder of (—)-11-O-ethylspergualin trihydrochloride in an overall yield of 17.1%; $[\alpha]_D^{25}-24.8°$ (c 1, water).

EXAMPLE 29

Synthesis of (—)-N-[4-(3-aminopropyl)aminobutyl]-2-(7-guanidinoheptanamido)-2-methoxyethanamide (a) (—)-N-[4-(3-benzyloxycarbonylaminopropyl)benzyloxycarbonylaminobutyl]-2-(7-guanidino-2-heptenamido)-2-methoxyethanamide Into 1.2 ml of N,N-dimethylformamide was dissolved 134.8 mg (0.187 mmole) of the (—)-1-N,4-bis(benzyloxycarbonyl)-11-O-methylspergualin hydrochloride obtained in Example 27(b). To the solution were added 192.9 mg (0.935 mmole) of dicyclohexylcarbodiimide and 5.6 mg of copper chloride (CuCl). The mixture was heated at 70° C. for 3 hours. After cooling, the precipitate was removed by filtration and the filtrate was concentrated under reduced pressure. The residue was dissolved in 5 ml of 30% aqueous methanol, adjusted to pH 7, passed through a column (80 ml) of Diaion ®HP-20, washed with 300 ml of water, then with 300 ml of 10% aqueous methanol and eluted with methanol. Fractions positive to Sakaguchi reaction were collected and concentrated under reduced pressure to obtain 114 mg of crude (—)-N-[4-(3-benzyloxycarbonylaminopropyl)-benzyloxycarbonylaminobutyl]-2-(7-guanidino-2-heptenamido)-2-methoxyethanamide hydrochloride which showed a signal of olefin proton at δ 6.02 in proton NMR spectrum (in deuteromethanol).

(b) (—)-N-[4-(3-aminopropyl)aminobutyl]-2-(7-guanidinoheptanamido)-2-methoxyethanamide Into a mixture of each 5 ml of methanol and water was dissolved 114 mg of the crude (—)-N-[4-(3-benzyloxycarbonylaminopropyl)benzyloxycarbonylaminobutyl]-2-(7-guanidino-2-heptenamido)-2-methoxyethanamide hydrochloride obtained above in (a). To the resulting solution were added 0.32 ml of 1N hydrochloric acid and 50 mg of 10% palladium-carbon. The mixture was stirred under a hydrogen stream for 1.5 hours at room temperature. The catalyst was removed by filtration and the filtrate was concentrated under reduced pressure. The residue was passed through a column of 100 ml of CM-Sephadex ®C-25 (Na-type) and fractionated by the gradient elution method with each 500 ml of water and 1M aqueous sodium chloride solution (fraction size, 10 g). Fractions No. 69 to No. 74 were combined, concentrated under reduced pressure and extracted three times with 5 ml of methanol. The methanol layer was passed through a column (150 ml) of Sephadex ®LH-20 and eluted with methanol to effect desalting (fraction size, 5 g). Fractions No. 16 to No. 21 were combined and evaporated to dryness to obtain 17.4 mg of a white powder of (—)-N-[4-(3-aminopropyl)aminobutyl]-2-(7-guanidinoheptanamido)-2-methoxyethanamide trihydrochloride; overall yield, 16.7%; $[\alpha]_D^{25}-30.4°$ (c 1, water).

We claim:

1. An N-[4-(3-aminopropyl)aminobutyl]-2-(ω-guanidinofatty-acid-amido)-2-substituted-ethanamide represented by the general formula or a pharmaceutically acceptable salt thereof

I

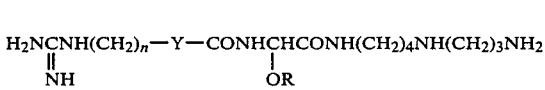

wherein Y represents —CH$_2$—CH$_2$—, or —CH=CH—, R represents a hydrogen atom, or a methyl group, and n is an integer of from 4 to 6.

2. The compound of claim 1 wherein R is the methyl group.

3. The compound of claim 1 wherein R represents hydrogen.

4. N-[4-(3-Aminopropyl)aminobutyl]-2-(7-guanidino-2-heptenamido)-2-hydroxyethanamide or a salt thereof.

5. N-[4-(3-Aminopropyl)aminobutyl]-2-(9-guanidino-2-nonenamido)-2-hydroxyethanamide or a salt thereof.

6. N-[4-(3-aminopropyl)aminobutyl]-2-(7-guanidinoheptanamido)-2-methoxyethanamide or a salt thereof.

7. N-[4-(3-aminopropyl)aminobutyl]-2-(7-guanidino-2-heptenamido)-2-methoxyethanamide or a salt thereof.

8. N-[4-(3-aminopropyl)aminobutyl]-2-(9-guanidinononanamido)-2-methoxyethanamide or a salt thereof.

9. N-[4-(3-aminopropyl)aminobutyl]-2-(7-guanidinoheptanamido)-2-hydroxyethanamide or a salt thereof.

10. N-[4-(3-aminopropyl)aminobutyl]-2-(9-guanidinononanamido)-2-hydroxyethanamide or a salt thereof.

* * * * *